United States Patent
Li et al.

(10) Patent No.: US 11,969,454 B2
(45) Date of Patent: Apr. 30, 2024

(54) COMPOSITIONS AND METHODS FOR TREATING THE EYE

(71) Applicant: Johnson & Johnson Surgical Vision, Inc., Irvine, CA (US)

(72) Inventors: Wen-Hwa Ting Li, Cranbury, NJ (US); Khalid Mahmood, Lawrenceville, NJ (US); Ramine Parsa, Lawrenceville, NJ (US); Mingqi Bai, Jacksonville, FL (US); Kenneth T. Holeva, Ponte Vedra Beach, FL (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 130 days.

(21) Appl. No.: 17/099,166

(22) Filed: Nov. 16, 2020

(65) Prior Publication Data
US 2021/0145916 A1    May 20, 2021

Related U.S. Application Data

(60) Provisional application No. 62/937,450, filed on Nov. 19, 2019, provisional application No. 62/937,467, filed on Nov. 19, 2019.

(51) Int. Cl.
| | | |
|---|---|---|
| *A61K 36/75* | (2006.01) |
| *A61K 9/08* | (2006.01) |
| *A61K 9/107* | (2006.01) |
| *A61K 31/192* | (2006.01) |
| *A61K 31/202* | (2006.01) |
| *A61K 31/728* | (2006.01) |
| *A61K 35/74* | (2015.01) |
| *A61K 36/28* | (2006.01) |
| *A61K 36/48* | (2006.01) |
| *A61K 36/54* | (2006.01) |
| *A61K 47/02* | (2006.01) |
| *A61K 47/26* | (2006.01) |
| *A61K 47/34* | (2017.01) |
| *A61P 27/04* | (2006.01) |

(52) U.S. Cl.
CPC ........... *A61K 36/75* (2013.01); *A61K 9/08* (2013.01); *A61K 9/1075* (2013.01); *A61K 31/192* (2013.01); *A61K 31/202* (2013.01); *A61K 31/728* (2013.01); *A61K 35/74* (2013.01); *A61K 36/28* (2013.01); *A61K 36/48* (2013.01); *A61K 36/54* (2013.01); *A61K 47/02* (2013.01); *A61K 47/26* (2013.01); *A61K 47/34* (2013.01); *A61P 27/04* (2018.01)

(58) Field of Classification Search
None
See application file for complete search history.

(56) References Cited

U.S. PATENT DOCUMENTS

| | | |
|---|---|---|
| 4,193,931 A | 3/1980 | Loeliger |
| 4,691,820 A | 9/1987 | Martinez |
| 4,939,171 A | 7/1990 | Moeller et al. |
| 5,467,868 A | 11/1995 | Abrams et al. |
| 5,488,815 A | 2/1996 | Abrams et al. |
| 5,561,109 A | 10/1996 | Mita et al. |
| 5,577,367 A | 11/1996 | Abrams et al. |
| 5,578,312 A | 11/1996 | Parrinello |
| 5,696,686 A | 12/1997 | Sanka et al. |
| 5,704,468 A | 1/1998 | Lust et al. |
| 5,823,327 A | 10/1998 | Wu et al. |
| 6,018,931 A | 2/2000 | Byram et al. |
| 6,050,398 A | 4/2000 | Wilde et al. |
| 6,071,962 A | 6/2000 | Ptchelintsev et al. |
| D435,966 S | 1/2001 | Duis et al. |
| 6,200,594 B1 | 3/2001 | Ernest et al. |
| 7,205,012 B1 | 4/2007 | Hill |
| 7,442,391 B2 | 10/2008 | Koganov |
| 7,452,547 B2 | 11/2008 | Lambino et al. |
| 7,473,435 B2 | 1/2009 | Koganov |
| 7,537,791 B2 | 5/2009 | Koganov |
| 8,128,973 B2 | 3/2012 | Mulvanerty |
| 8,361,516 B2 | 1/2013 | Lintner et al. |
| 8,496,976 B2 | 7/2013 | Gore et al. |
| 8,828,412 B2 | 9/2014 | Yu et al. |
| 9,220,928 B2 | 12/2015 | Gordon et al. |
| 9,364,414 B2 | 6/2016 | Domloge et al. |
| 9,480,645 B2 | 11/2016 | Yu |
| 9,814,659 B2 | 11/2017 | Loy et al. |
| 9,925,137 B2 | 3/2018 | Stout et al. |
| 10,010,572 B2 | 7/2018 | Parris |
| 10,966,948 B2 | 4/2021 | Li et al. |
| 11,197,841 B2 | 12/2021 | Li et al. |
| 2003/0113388 A1 | 6/2003 | Phan |
| 2003/0165545 A1 | 9/2003 | Huth et al. |

(Continued)

FOREIGN PATENT DOCUMENTS

| | | |
|---|---|---|
| CA | 2739658 A1 | 4/2010 |
| CA | 2617255 C | 4/2016 |

(Continued)

OTHER PUBLICATIONS

Belikov, V.G., Pharmaceutical Chemistry, Moscow, Vysshaya Shkola, 1993, pp. 43-47. (Machine Translation).

(Continued)

*Primary Examiner* — Michael Barker
(74) *Attorney, Agent, or Firm* — Johnson & Johnson Surgical Vision, Inc.

(57) ABSTRACT

The present invention relates to compositions comprising one or more extracts and/or compounds having retinol-like activity and properties and methods of using the compositions to treat the eye.

16 Claims, 6 Drawing Sheets

(56) References Cited

U.S. PATENT DOCUMENTS

| | | |
|---|---|---|
| 2004/0146539 A1 | 7/2004 | Gupta |
| 2004/0156873 A1 | 8/2004 | Gupta |
| 2004/0161435 A1 | 8/2004 | Gupta |
| 2004/0202638 A1 | 10/2004 | Takada et al. |
| 2004/0223942 A1 | 11/2004 | Fujimura |
| 2005/0226834 A1 | 10/2005 | Bambino et al. |
| 2005/0238613 A1 | 10/2005 | Cals-Grierson et al. |
| 2006/0110415 A1 | 5/2006 | Gupta |
| 2006/0133997 A1 | 6/2006 | Querleux et al. |
| 2008/0221064 A1 | 9/2008 | Ueno et al. |
| 2009/0241242 A1 | 10/2009 | Beatty et al. |
| 2010/0190734 A1 | 7/2010 | Brazzell et al. |
| 2011/0077219 A1 | 3/2011 | Conti |
| 2011/0318439 A1 | 12/2011 | Gordon et al. |
| 2012/0003296 A1 | 1/2012 | Shantha et al. |
| 2013/0195925 A1 | 8/2013 | Arshed |
| 2013/0259815 A1 | 10/2013 | Loy et al. |
| 2015/0250691 A1 | 9/2015 | Piccardi et al. |
| 2016/0000845 A1 | 1/2016 | Olsen |
| 2016/0074455 A1 | 3/2016 | Paufique |
| 2017/0049719 A1 | 2/2017 | Marcy et al. |
| 2017/0172964 A1 | 6/2017 | Coupland |
| 2017/0304187 A1 | 10/2017 | Weisenfluh et al. |
| 2018/0036233 A1 | 2/2018 | Shabaik et al. |
| 2018/0161263 A1 | 6/2018 | Au et al. |
| 2019/0008907 A1 | 1/2019 | Al-Waili |
| 2019/0091122 A1 | 3/2019 | Brun et al. |
| 2019/0105261 A1 | 4/2019 | Waugh et al. |
| 2021/0186913 A1 | 6/2021 | Li et al. |
| 2022/0087965 A1 | 3/2022 | Li et al. |

FOREIGN PATENT DOCUMENTS

| | | |
|---|---|---|
| CN | 101336869 A | 1/2009 |
| CN | 101376016 | 3/2009 |
| CN | 101411679 A | 4/2009 |
| CN | 102307842 A | 1/2012 |
| CN | 103417391 A | 12/2013 |
| CN | 103505389 B | 1/2014 |
| CN | 103142968 B | 2/2014 |
| CN | 104042540 A | 9/2014 |
| CN | 105411960 A | 3/2016 |
| CN | 106176275 B | 12/2016 |
| CN | 108852985 A | 11/2018 |
| CN | 109833267 A | 6/2019 |
| EP | 0 334 777 A1 | 9/1989 |
| EP | 742007 A1 | 11/1996 |
| EP | 904772 B1 | 9/2003 |
| EP | 1303253 B1 | 9/2004 |
| EP | 2254544 B1 | 1/2012 |
| JP | H08133967 A | 5/1996 |
| JP | 2001151633 A | 6/2001 |
| JP | 2003002813 A | 1/2003 |
| JP | 2003137767 A | 5/2003 |
| JP | 2003238432 A | 8/2003 |
| JP | 2005132793 A | 5/2005 |
| JP | 2006008537 A | 1/2006 |
| JP | 2006063038 A | 3/2006 |
| JP | 2006273811 A | 10/2006 |
| JP | 2009013128 | 1/2009 |
| JP | 4278473 B2 | 6/2009 |
| JP | 2010106000 A | 5/2010 |
| KR | 2006074038 A | 7/2006 |
| KR | 2016009330 A | 1/2016 |
| KR | 2016109360 A | 9/2016 |
| KR | 2016116733 A | 10/2016 |
| KR | 2017012810 A | 2/2017 |
| MX | 2011/013407 A | 6/2013 |
| RO | 115698 B1 | 3/2002 |
| RU | 2292887 C2 | 2/2007 |
| RU | 2014140541 | 1/2015 |
| WO | WO 1997/004788 A | 2/1997 |
| WO | WO 97/39769 A1 | 10/1997 |
| WO | WO 2002015860 A1 | 2/2002 |
| WO | WO 2005034917 A2 | 4/2005 |
| WO | WO 2005/049048 A1 | 6/2005 |
| WO | WO 2005049048 A1 | 6/2005 |
| WO | 2007061200 A1 | 5/2007 |
| WO | WO 2010/071941 A1 | 1/2010 |
| WO | WO 2010/111745 A1 | 10/2010 |
| WO | WO 2013/171764 A2 | 11/2013 |
| WO | WO 2013/171764 A3 | 11/2013 |
| WO | 2015099019 A1 | 7/2015 |
| WO | WO 2017013568 A1 | 1/2017 |
| WO | 2017053339 A1 | 3/2017 |
| WO | WO 2017219582 A1 | 12/2017 |
| WO | WO 2018154145 A2 | 8/2018 |
| WO | WO 2018154145 A3 | 8/2018 |
| WO | WO 2019075263 A2 | 4/2019 |
| WO | WO 2020/021475 A2 | 1/2020 |
| WO | WO 2020/021477 A2 | 1/2020 |
| WO | WO 2020/021480 A2 | 1/2020 |

OTHER PUBLICATIONS

Kharkevich, D.A., Pharmacology: Textbook, $9^{th}$ Edition, revised and corrected, Moscow, GEOTAR Media, 2008, pp. 66-67. (Machine Translation).

Epifano, F., et al., Phytochemistry and pharmacognosy of the genus Acronychia, Phytochemistry, 2013, 95:12-8, Abstract.

Bowen, P., "Particle Size Distribution Measurement from Millimeters to Nanometers and from Rods to Platelets," Journal of Dispersion Science and Technology, Taylor and Francis Group, New York, NY, vol. 23, No. 5, Jan. 1, 2002, pp. 631-662. (XP009102859).

Extended EP Search Report, EP 20208677.3-1112, dated Apr. 15, 2021.

Belikov V.G., "Pharmaceutical Chemistry," Textbook, 2007, Moscow, MEDpress Information, pp. 27-29.

Gupta S.K., et al., "Trigonella Foenum-graecum (Fenugreek) Protects Against Selenite-induced Oxidative Stress in Experimental Cataractogenesis," Biological Trace Element Research, Sep. 2010, vol. 136 (3), pp. 258-268.

Amiram El-Ganiny, et al.; "Prevention of Bacterial Biofilm Formation on Soft Contact Lenses Using Natural Compounds"; Journal of Ophthalmic Inflammation and Infection; BioMed Central Ltd.; vol. 7, No. 1, Apr. 18, 2017; pp. 1-7.

Blavin, Julia et al., "A Comparison of Azithromycin and Tobramycin Eye Drops on Epithelial Wound Healing and Tolerance After Penetrating Keratoplasty," Journal of Ocular Pharmacology and Therapeutics, vol. 28, No. 4, Aug. 1, 2012, pp. 428-432.

Colipa Guideline: Guideline for the Colorimetric Determination of Skin Colour Typing and Prediction of the Minimal Erythemal Dose (MED) Without UV Exposure (2007).

Craig, J.P. et al. TFOS DEWS II definition and classification report. *Ocul Surf.* 2017; 15:276-283.

David A. Leigh et al. Angew. Chem Int. Ed., 2001, 40, No. 8, pp. 1538-1542.

De Silva et al., "Demethylacrovestone From Achronychia Pedunculata Fruits", Phytochemistry, (1991), 30(5), pp. 1709-1710.

Dominique Lesueur, et al.; Composition and antimicrobial activity of the essential oil of *Acronychia pedunculata*; (L.) Miq.; Natural Product Research; vol. 22, vol. 5, Mar. 20, 2008; pp. 393-398.

Dreyfuss JL, Regatieri CV, Coelho B, et al. Altered hyaluronic acid content in tear fluid of patients with adenoviral conjunctivitis. An Acad Bras Cienc. 2015;87(1):455 462.

Driot, J.Y. et al., Beneficial effects of a retinoic acid analog, CBS-211 A, on an experimental model of keratoconjunctivitis sicca, Investigative ophthalmology & visual science, Jan. 1, 1992, p. 190.

Efstratiou, Efstratios, et al., "Antimicrobial activity of petal extracts against fungi, as well as Gram-negative and Gram-positive clinical pathogens," Complementary Therapies in Clinical Practice, vol. 18, No. 3, 2012, pp. 173-176.

"Elma Skin Revitalizer, accessed before Jul. 23, 2019 https://elmaskincare.com/files/P_HT-ELMASR.htm.".

Elmallah Mohammed I Y et al., "Marine actinomycete crude extracts with potent TRAIL-resistance overcoming activity against breast cancer cells." Oncology Reports Jun. 2017, vol. 37, No. 6, pp. 3635-3642.

(56) References Cited

OTHER PUBLICATIONS

El-Nekeety Aziza A et al., "Evaluation of the bioactive extract of actinomyces isolated from the Egyptian environment against aflatoxin B1-induce cytotoxicity, genotoxicity and oxidative stress in the liver of rats." Food and Chemical Toxicology, Pergamon, GB, vol. 105, Apr. 23, 2017 pp. 241-255.
Eric Carlson, et al.; "Impact of Hyaluronic Acid-Containing Artificial Tear Products on Reepithelialization in an In Vivo Corneal Wound Model"; Journal of Ocular Pharmacology and Therapeutics; vol. 34, No. 4, May 1, 2018; pp. 360-364.
Extracts of *Calendula officinalis* and of *Trigonella foenum-graecum* can be obtained from Caithness Biotechnologies Ltd, UK (http://www.caithnessbiotechnologies.com/); http://caithnessbiotechnologies.com/contact.html/.
Gagliano, Caterina, et al., "ARVO Annual Meeting Abstract: Effect of Fenugreek on Severe Evaporative Dysfunctional Tear Syndrome, IOVS, ARVO Journals," Investigative Ophthalmology and Visual Science, Mar. 1, 2012, p. 2, paragraph 1; figure 1.
Himejima, Masaki, et al., "Antimicrobial Agents from Licaria puchuri-major and Their Synergistic Effect with Polygodial," Journal of Natural Products, vol. 55, No. 5, May 1, 1992, pp. 620-625.
International Cosmetic Ingredient Dictionary and Handbook, eds. Wenninger and McEwen, pp. 1626, 1654-61, and 1673-1686 (The Cosmestic, Toiletry and Fragrance Assoc., Washington, D.C.), 7th Edition, 1997.
International Search Report, PCT/IB2019/056335; dated Jan. 31, 2020.
International Search Report, PCT/IB2019/056337 dated Mar. 20, 2020.
International Search Report, PCT/IB2019/056344 dated Nov. 3, 2020.
Invitation to Pay Additional Fees/Partial International Search Report PCT/IB2019/056344 dated Nov. 28, 2019.
Invitation to Pay Additional Fees/Partial International Search Report PCT/IB2019/056337 dated Nov. 27, 2019.
Jean-Claude Chambron et al. Pure & Appl. Chem., 1990, vol. 62, No. 6, pp. 1027-1034.
Kaercher T., et al.; "The use of compresses as a supplementary therapy for hyposecretory and hyperevaporative keratoconjunctivitis sicca"; Spektrum Der Augenheilkunde; vol. 16, No. 4, Aug. 1, 2002; pp. 164-169.
Laemmli UK. 1970. Cleavage of structural proteins during the assembly of the head of bacteriophage T4, Nature 227: 680-685.
Li, et al.; "In vitro modeling of unsaturated free fatty acid-mediated tissue impairments seen in acne lesions", Arch Dermatol Res, published on May 31, 2017, Springer-Verlag Berlin Heidelbert 2017.
Loeliger, P., et al., "Arotinoids, A New Class of Highly Active Retinoids," European Journal of Medicinal Chemistry, vol. 15, No. 1, Jan. 1, 1980, pp. 9-15.
Lucas Meyer; "SouthernCross Botanicals," Nov. 19, 2014, pp. 1-20 retrieved from Internet: https://in-cosmetics.com/_novadocuments/245955?v=636017775273900000.
Maker AV, Katabi N, Gonen M, et al. Pancreatic cyst fluid and serum mucin levels predict dysplasia in intraductal papillary mucinous neoplasms of the pancreas. *Ann Surg Oncol.* 2011;18(1):199-206.
Martins Jr, Passerotti CC, Maciel RM, Sampaio Lo, Dietrich CP and Nader HB. 2003.) Practical determination of hyaluronan by a new noncompetitive fluorescence-based assay on serum of normal and cinhotic patients. Anal Biochem 319: 65-72.
Mintel—Aug. 26, 2009—"Eye Drops.".
Mintel—Feb. 14, 2011, "2/1 Eye Cream.".
Mintel—Feb. 14, 2011, "Sleeping Mask.".
Mintel—Fruit Fiesta Peel, MyChelle Dermaceuticals Age Defense, Apr. 2012.
Mintel—Jun. 28, 2007, "Loaded The Anti-Ager.".
Mintel—May 22, 2017, "Sensitive Body Lotion.".
Muhammad Nadeem Aslam, et al. "Padma 28: A Multi-Component Herbal Preparation with Retinoid-Like Dermal Activity but Without Epidermal Effects," Journal of Investigative Dermatology; vol. 124, No. 3, Mar. 1, 2005, pp. 524-529.
Pacella, E., Pascella, F., De Paolis, G., et al. *Glycosaminoglycans in the human cornea: age-related changes.* Ophthalmol. Eye Dis. 7:1-5, 2015).
Ratan Chaudhuri: "Bakuchiol: A Retinol-Like Functional Compound, Modulating Multiple Retinol and Non-Retinol Targets" In: "Cosmeceuticals and Active Cosmetics, Third Edition," Aug. 27, 2015.
Scuderi, Gianluca et al., "Effects of phytoestrogen supplementation in postmenopausal women with dry eye syndrome: a randomized clinical trial," Canadian Journal of Ophthalmology, vol. 47, No. 6, Dec. 1, 2012, pp. 489-492.
Shizuka Koh; "Clinical utility of 3% diquafosol ophthalmic solution in the treatment of dry eyes"; Clinal Ophthalmology; May 1, 2015, p. 865.
Skinlightco.uk: "Skin Brightening Fruit Fiesta Peel," (URL:http://www.skinlight.co.uk/product_845_Skin+Brightening+Fruit+Fiesta+Peel+.html —Jan. 1, 2006).
Solano et al., "Hypopigmenting Agents: an updated review on biological, chemical and clinical aspects", Pigment Cell Research, vol. 19, No. 6, Dec. 1, 2006, pp. 550-571, XP0906-9305, ISSN: 0906-9305 DOI:10.1111/J.1600-0749.2006.00334.X; Retrieved from the Internet: URL:http://leenyx.icecreamlovestheweb.com/backend/media/54201093909AM/Hypopigmenting%20agents%20an%20Oupdated%20review%20on.pdf [retrieved on Aug. 8, 2006].
Su et al., "Acetophenone Derivatives from Acronychia pedunculata", Journal of Natural Products, (2003), 66(7) pp. 990-993.
Takemura Maki et al., "Canaliculitis caused by Actinomyces in a case of dry eye with punctal plug occlusion." Nippon Ganka Gakkai Zasshi Jul. 2002, vol. 106, No. 7, pp. 416-419.
Tanimoto, Shinichi et al., "Synthesis and Cosmetic Whitening Effect of Glycosides Derived from Several Phenylpropanoids", Yakugaku Zasshi=Journal of the Pharmaceutical Society of Japan, JP, vol. 126, No. 3, Mar. 1, 2006, pp. 173-177, XP009081014, ISSN: 0031-6903, DOI:10.1248/Yakushi. 126.173.
Toshida, H., et al.; The Effects of Vitamin A Compound on Hyaluronic Acid Released from Cultured Rabbit Corneal Epithelial Cells and Keratocytes, J Nutr Sci Vitaminol, 58, pp. 223-229 (2012).
Toshida, Hiroshi et al., "Efficacy of retinol palmitate eye drops for dry eye in rabbits with lacrimal gland resection," Clinical Ophthalmology, Oct. 1, 2012, p. 1585.
Uchino Y, Uchino M, Yokoi N, et al. Alteration of Tear Mucin 5AC in Office Workers Using Visual Display Terminals: The Osaka Study. *JAMA Ophthalmol.* n2014;132(8):985-992.
Zuo Xia Lin et al., "Application of Free Radical Scavenger in Cosmetics", the 11th Southeast Asia Cosmetic Medicine Academic Conference, pp. 29-31, Dec. 31, 2009 (Reference translation—may contain inconsistencies).
Lee C., et al., "Inhibition of *Streptococcus Pyogenes* Growth by Native Australian Plants: New Approaches Towards the Management of Impetigo, Pharyngitis and Rheumatic Heart Disease," Pharmacognosy Communications, Jul. 2016, vol. 6(3), pp. 164-173.

*p < 0.05 vs untreated (UT)

COMPOSITIONS AND METHODS FOR TREATING THE EYE

CROSS REFERENCE TO RELATED APPLICATION

The present application claims the benefit of the earlier filing date of U.S. provisional patent applications 62/937,450 and 62/937,467, each, filed Nov. 19, 2019, the entirety of each such application is hereby incorporated by reference herein as if fully set forth herein.

FIELD OF THE INVENTION

The present invention relates to compositions comprising one or more extracts and/or compounds having retinol-like activity and properties and methods of using the compositions to treat the eye.

BACKGROUND OF THE INVENTION

"Dry eye is a multifactorial disease of the ocular surface characterized by a loss of homeostasis of the tear film, and accompanied by ocular symptoms, in which tear film instability and hyperosmolarity, ocular surface inflammation and damage, and neurosensory abnormalities play etiological roles." Craig, J. P. et al. TFOS DEWS II definition and classification report. *Ocul Surf.* 2017; 15: 276-283. Dry eye can result from abnormal or inadequate tear formation, and deficiency in mucin secretion (i.e., keratoconjunctivitis sicca). Dry eye symptoms can be manifest as a result of various underlying disorders such as autoimmune disorders that damage lacrimal (i.e., tear-producing) glands, such as rheumatoid arthritis, Sjögren's syndrome, systemic lupus erythematosus, and systemic sclerosis and sarcoidosis. Dry eye can also be induced following eye surgery, such as Lasik® surgery. Dry eye is estimated to affect more than 13 million individuals in the United States.

Regardless of the underlying pathology, dry eye commonly involves the rapid breakdown of the pre-ocular tear film, resulting in dehydration of the exposed outer surface. Normal tear formation is required to keep the cornea and conjunctiva moist, and this in turn helps to prevent ulceration of both, as well as to maintain corneal transparency. In addition, tears facilitate movement of the eyelid over the eye surface (e.g., blinking) and removal of foreign substances from the eye. Tears also normally contain lysozyme which is useful in preventing infection in the eye. Dry eye can be associated with mild discomfort to severe pain in the eye. When it occurs for prolonged periods of time, it can cause blurred vision, grittiness and/or burning sensation, and itchiness. If the condition is allowed to persist without treatment, it can further lead to corneal ulcers and/or scarring.

Dry eye symptoms include eye pain or fatigue, increased blinking, and bloodshot eyes. Further, bacteria may enter through a scratch and cause infection, and if the scratch is deep enough it can even affect the vision of the person. In addition to eyestrain, causes of dry eye include Sjogren's syndrome, Stevens-Johnson syndrome, burns and injury to the eye, and side effects of hypotensive drugs, tranquilizers, eyedrops for treating glaucoma, and other such drugs.

Eyedrops are an effective way to treat dry eye. Such eyedrops typically include dry-eye treatment actives—a common active in such eyedrops is hyaluronic acid. Hyaluronic acid is a biologically derived macromolecular substance, has extremely high water retention and characteristic properties such as high viscoelasticity, good thickening properties, and good thread-forming ability, and has been used as a humectant in topical agents for treating various kinds of skin problems and so forth. In the case of dry eye caused by Sjogren's syndrome, in which dryness is seen over' the entire body, the application of eyedrops containing hyaluronic acid is effective. However, when instilled as an eyedrop, hyaluronic acid has a relatively short residence time on the cornea, so the effect of hyaluronic acid eyedrops lasts only about 2 or 3 hours, which means that the patient must apply the drops more frequently (such as 5 to 10 times a day).

Hyaluronic acid (HA) is produced by corneal epithelial cells in the eye. Notably, significantly higher hyaluronic acid concentrations have been found in the corneas of younger human population than in the older. (See Pacella, E., Pascella, F., De Paolis, G., et al. *Glycosaminoglycans in the human cornea: age-related changes*. Ophthalmol. Eye Dis. 7:1-5, 2015).

In addition, the tear film is the body's natural defense against dry eye. The tear film contains ocular mucins and is essential for maintaining the homeostasis of the wet ocular surface. Mucins are produced, among other places, by corneal epithelial cells in the eye. Mucins are glycoproteins expressed by epithelial tissues of mucosal surfaces. They protect tissues by functioning as antioxidants and providing lubrication. Mucin genes associated with the tear film include MUC1, MUC2, MUC4, MUC5AC, MUC5B, MUC7 and MUC16.

Mucin is also useful as an antimicrobial and both Mucin and hyaluronic acid are useful for general wound healing, and is essential for overall eye health maintenance.

There is therefore a need for an ophthalmic pharmaceutical composition that would promote and/or improve the production and/or release of hyaluronic acid and/or mucin from and/or in the cornea.

The present inventors have discovered compounds and/or extracts having retinol-like properties and/or benefits which can induce, promote and/or improve production/release/delivery/excretion of hyaluronic acid and/or mucin from and/or in the cornea.

Accordingly, an aspect of the present invention relates to compositions comprising a safe and effective amount of one or more compounds and/or extracts having retinol-like properties and/or benefits for treating dry eye.

Another aspect of the present invention relates to microemulsion compositions comprising a safe and effective amount of one or more compounds and/or extracts having retinol-like properties and/or benefits to induce, promote and/or improve the production/release/delivery/excretion of hyaluronic acid and/or mucin from and/or in the cornea.

Another aspect of the present invention relates to methods of preventing and/or treating (e.g., reducing) eye symptoms associated with dry eye and/or resulting from decreased or low-level production/release/delivery/excretion of hyaluronic acid and/or mucin from and/or in the cornea by administering compositions comprising a safe and effective amount of one or more compounds and/or extracts having retinol-like properties and/or benefits.

Specifically, one aspect of the present invention relates to compositions comprising safe and effective amount of one or more compounds and/or extracts having retinol-like properties and/or benefits to induce, promote and/or improve production/release/delivery/excretion of hyaluronic acid and/or mucin from and/or in the cornea, which compositions can be administered to patients having a hyaluronic acid concentration, in their tears, lower than 10 (or about 10) nanograms, optionally lower than 15 (or about 15) nanograms, optionally lower than 20 (or about 20) nanograms, or optionally lower than 25 (or about 25) nanograms, per milligram of proteins, such that the concentration of hyaluronic acid in their tears is raised to (or, is made to be) equal to or greater than 10 (or about 10), optionally equal to or greater than 15 (or about 15), optionally equal to or greater than 20 (or about 20), optionally equal to or greater than 25 (or about 25) nanograms, optionally equal to or greater than 30 (or about 30), optionally equal to or greater than 35 (or about 35), optionally equal to or greater than 40 (or about 40), or optionally equal to or greater than 45 (or about 45) nanograms per milligram of proteins to 100 (or about 100), optionally 90 (or about 90), optionally 80 (or about 80), optionally 70 (or about 70), or optionally 60 (or about 60) nanograms per milligram of proteins.

In certain embodiments, the above-described concentration of hyaluronic acid, in the patients' tears, resulting from the compounds and/or extracts having retinol-like properties and/or benefits is maintained for a period of up to, at least, about 2 hours, optionally about 4 hours, optionally about 6 hours, optionally about 8 hours, optionally about 10 hours, optionally about 12 hours, or optionally from about 12 to about 24 hours.

Concentrations of hyaluronic acid detailed above are determined using the Dreyfuss Method (described below in the definitions).

A similar aspect of the present invention relates to compositions comprising a safe and effective amount of safe and effective amount of one or more compounds and/or extracts having retinol-like properties and/or benefits to induce, promote and/or improve production/release/delivery/excretion of hyaluronic acid from and/or mucin in the cornea, which compositions can be administered to patients having a MUC5AC concentration in tears lower than 6 (or about 6), optionally 8 (or about 8), nanograms per milligram of proteins, such that the concentration of MUC5AC in the tears is raised to (or, is made to be) equal to or greater than 8 (or about 8) nanograms to 15 (or about 15) nanograms, optionally from 9 (or about 9) nanograms to 12 (or about 12) nanograms, per milligram of proteins.

In certain embodiments, the above-described concentration of MUC5AC in the tears (i.e., equal to or greater than 8 (or about 8) nanograms to 15 (or about 15) nanograms, optionally from 9 (or about 9) nanograms to 12 (or about 12) nanograms, per milligram of proteins), resulting from the compounds and/or extracts having retinol-like properties and/or benefits to induce, promote and/or improve production/release/delivery/excretion of hyaluronic acid and mucin from and/or in the cornea is maintained for a period of up to, at least, about 2 hours, optionally about 4 hours, optionally about 6 hours, optionally about 8 hours, optionally about 10 hours, optionally about 12 hours, or optionally from about 12 to about 24 hours.

Concentrations of MUC5AC in tears detailed above are determined using the Uchino Method (described below in the definitions).

A further aspect of the present invention relates to methods of promoting healing or increasing the rate of healing of wounds in and/or on the eye (e.g., non-dry eye associated, eye trauma, postoperative surgical or nonspecific wounds) of a patient by administering compositions comprising a safe and effective amount of one or more compounds and/or extracts having retinol-like properties and/or benefits to induce, promote and/or improve production/release/delivery/excretion of hyaluronic acid or mucin from and/or in the cornea (namely, to increase production/release/delivery/excretion of hyaluronic acid or mucin from and/or in the cornea), in certain embodiments, beyond the respective concentration levels of hyaluronic acid or mucin ordinarily produced by such patient without (or absent) administration of the compositions comprising a safe and effective amount of one or more compounds and/or extracts having retinol-like properties and/or benefits).

A still further aspect of the present invention relates to methods for improving the antimicrobial properties in tears (or, the tear film of the eye) of a patient by administering compositions comprising a safe and effective amount of one or more compounds and/or extracts having retinol-like properties and/or benefits to induce, promote and/or improve production/release/delivery/excretion of hyaluronic acid and/or mucin from and/or in the cornea (namely, to increase production/release/delivery/excretion of mucin from and/or in the cornea, in certain embodiments, beyond the concentration level of mucin ordinarily produced by such patient without (or absent) the administration of the compositions comprising a safe and effective amount of such one or more compounds and/or extracts having retinol-like properties and/or benefits).

SUMMARY OF THE INVENTION

The present invention relates to microemulsion compositions for treating the eye comprising:
i) a safe and effective amount of a compound and/or extract having retinol-like properties and/or benefits for use in treating the eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

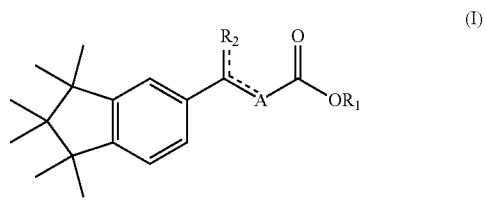

wherein—
the dotted lines represent simple or double bound; optionally one of the dotted line is a double bound;
$R_1$ represent an H, a carbonated chain, linear, cyclic, or branched, saturated or unsaturated, comprising from 1 to 20 carbon atoms;
$R_2$ represent a carbonated chain, linear, cyclic ringed, or branched, saturated or unsaturated, comprising from 1 to 20 carbon atoms; optionally a methyl ($—CH_3$) or methylene ($=CH_2$) moiety; a carbonated chain, linear, ringed, or branched, saturated or unsaturated, comprising from 1 to 20 carbon atoms; optionally from 1 to 10 carbon atoms; optionally 6 carbon atoms; optionally an aromatic moiety, optionally a phenyl moiety; optionally 2-methyl-prop-1,3-diene; and
ii) an ophthalmologically acceptable carrier,
wherein the microemulsion droplets or particles have a maximum dimension of less than 1,500 Å.

The present invention relates to methods for preventing or treating the symptoms associated with dry eye (optionally, in a patient in need of such prevention and treatment) of comprising the step of administering a microemulsion composition comprising:

i) a safe and effective amount of a compound and/or extract having retinol-like properties and/or benefits for use in treating dry eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

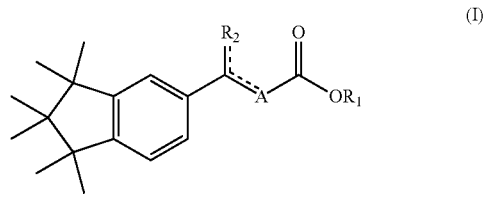

(I)

wherein—
the dotted lines represent simple or double bound; optionally one of the dotted line is a double bound;
$R_1$ represent an H, a carbonated chain, linear, cyclic, or branched, saturated or unsaturated, comprising from 1 to 20 carbon atoms;
$R_2$ represent a carbonated chain, linear, cyclic ringed, or branched, saturated or unsaturated, comprising from 1 to 20 carbon atoms; optionally a methyl (—$CH_3$) or methylene (=$CH_2$) moiety; a carbonated chain, linear, ringed, or branched, saturated or unsaturated, comprising from 1 to 20 carbon atoms; optionally from 1 to 10 carbon atoms; optionally 6 carbon atoms; optionally an aromatic moiety, optionally a phenyl moiety; optionally 2-methyl-prop-1,3-diene; and ii) an ophthalmologically acceptable carrier, wherein the microemulsion droplets or particles have a maximum dimension of less than 1,500 Å.

The present invention relates to methods for treating a patient having decreased or low-level production/release/delivery/excretion of hyaluronic acid from and/or in the cornea comprising the step of topically administering to the eye the patient a microemulsion composition comprising:

i) a safe and effective amount of a compound and/or extract having retinol-like properties and/or benefits for use in treating dry eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

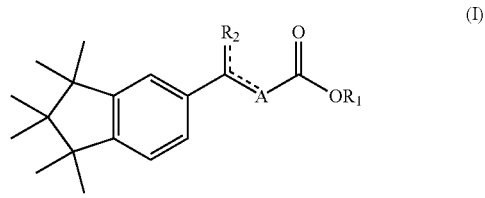

(I)

wherein—
the dotted lines represent simple or double bound; optionally one of the dotted line is a double bound;
$R_1$ represent an H, a carbonated chain, linear, cyclic, or branched, saturated or unsaturated, comprising from 1 to 20 carbon atoms;
$R_2$ represent a carbonated chain, linear, cyclic ringed, or branched, saturated or unsaturated, comprising from 1 to 20 carbon atoms; optionally a methyl (—$CH_3$) or methylene (=$CH_2$) moiety; a carbonated chain, linear, ringed, or branched, saturated or unsaturated, comprising from 1 to 20 carbon atoms; optionally from 1 to 10 carbon atoms; optionally 6 carbon atoms; optionally an aromatic moiety, optionally a phenyl moiety; optionally 2-methyl-prop-1,3-diene; and ii) optionally, an ophthalmologically acceptable carrier, wherein the microemulsion droplets or particles have a maximum dimension of less than 1,500 Å.

The present invention relates to methods for preventing or treating the symptoms associated with dry eye comprising the step of topically administering to a patient (optionally, in a patient need of such prevention or reduction in dry eye symptoms) a microemulsion composition comprising:

i) a safe and effective amount of a compound and/or extract having retinol-like properties and/or benefits for use in treating dry eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

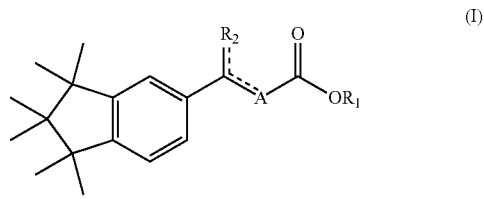

(I)

wherein—
the dotted lines represent simple or double bound; optionally one of the dotted line is a double bound;
$R_1$ represent an H, a carbonated chain, linear, cyclic, or branched, saturated or unsaturated, comprising from 1 to 20 carbon atoms;
$R_2$ represent a carbonated chain, linear, cyclic ringed, or branched, saturated or unsaturated, comprising from 1 to 20 carbon atoms; optionally a methyl (—$CH_3$) or methylene (=$CH_2$) moiety; a carbonated chain, linear, ringed, or branched, saturated or unsaturated, comprising from 1 to 20 carbon atoms; optionally from 1 to 10 carbon atoms; optionally 6 carbon atoms; optionally an aromatic moiety, optionally a phenyl moiety; optionally 2-methyl-prop-1,3-diene; and ii) optionally, an ophthalmologically acceptable carrier, wherein the microemulsion droplets or particles have a maximum dimension of less than 1,500 Å.

The present invention relates to methods for promoting healing or increasing the rate of healing of wounds in and/or on the eye of a patient (optionally, in a patient need of such eye wound healing) by administering compositions (i.e., which increase production/release/delivery/excretion of hyaluronic acid from and/or in the cornea, in certain embodiments, beyond the concentration level of hyaluronic acid produced by such patient without (or absent) administration of the emulsion compositions comprising a safe and effective amount of one or more compounds and/or extracts having retinol-like properties and/or benefits) comprising:
i) a safe and effective amount of a compound and/or extract having retinol-like properties and/or benefits for use in treating dry eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

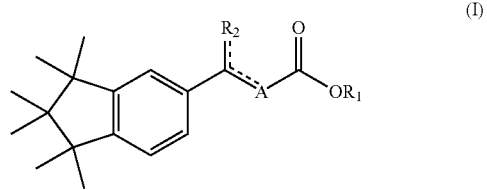

wherein—
the dotted lines represent simple or double bound; preferably one of the dotted line is a double bound;
$R_1$ represent an H, a carbonated chain, linear, cyclic, or branched, saturated or unsaturated, comprising from 1 to 20 carbon atoms;
$R_2$ represent a carbonated chain, linear, cyclic ringed, or branched, saturated or unsaturated, comprising from 1 to 20 carbon atoms; preferably a methyl (—$CH_3$) or methylene (=$CH_2$) moiety;
a represent a carbonated chain, linear, ringed, or branched, saturated or unsaturated, comprising from 1 to 20 carbon atoms; preferably from 1 to 10 carbon atoms; more preferably 6 carbon atoms; preferably an aromatic moiety, preferably a phenyl moiety; preferably 2-methyl-prop-1,3-diene.
ii) optionally, an ophthalmologically acceptable carrier, wherein the microemulsion droplets or particles have a maximum dimension of less than 1,500 Å.

DETAILED DESCRIPTION OF INVENTION

Figure 1:
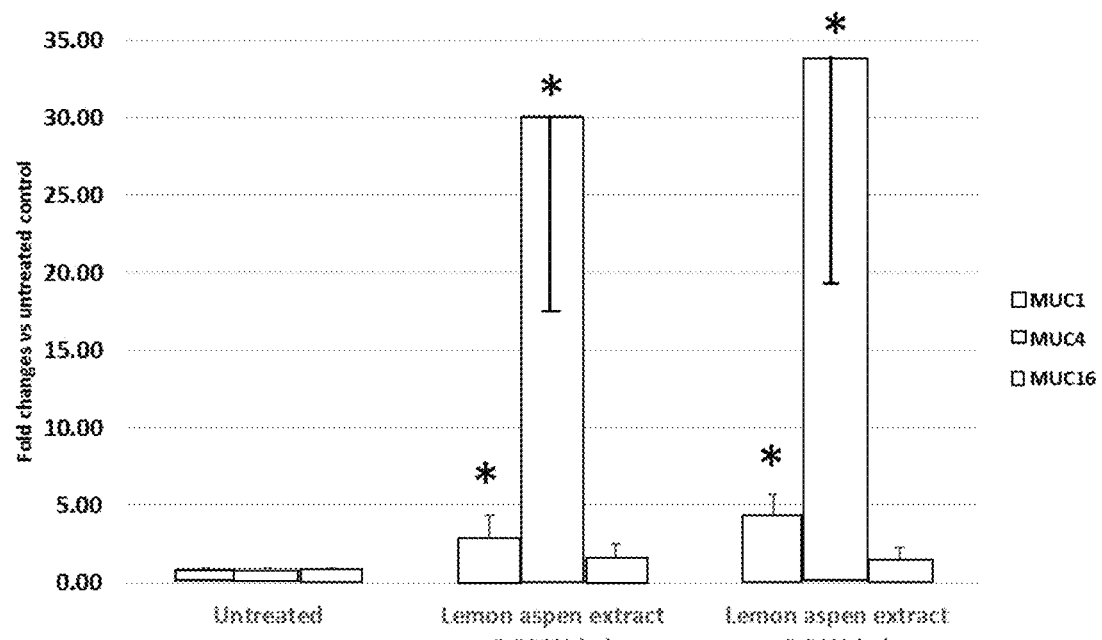
FIG. 1 depicts bar graphs showing lemon aspen extract induced MUC1, MUC4 and MUC16 gene expression in corneal epithelial cells.

It is believed that one skilled in the art can, based upon the description herein, utilize this invention to its fullest extent. The following specific embodiments can be construed as merely illustrative, and not limitative of the remainder of the disclosure in any way whatsoever.

The compositions of the present invention can comprise, consist of, or consist essentially of the elements, steps and limitations of the invention described herein, as well any of the additional or optional ingredients, components, or limitations described herein.

The term "comprising" (and its grammatical variations) as used herein is used in the inclusive sense of "having" or "including" and not in the exclusive sense of "consisting only of" The terms "a" and "the" as used herein are understood to encompass the plural as well as the singular.

Unless defined otherwise, all technical and scientific terms used herein have the same meaning as commonly understood by one of ordinary skill in the art to which the invention belongs. Also, all publications, patent applications, patents, and other references mentioned herein are incorporated by reference in their entirety to the extent that they are not inconsistent with this specification. As used herein, all percentages are by weight of the total composition unless otherwise specified.

As used herein, the terms "cornea" or "corneal" is, includes and/or relates to, the transparent front part of the eye that covers the iris, pupil, and anterior chamber, the layers of which transparent front part include the corneal epithelium layer (comprising corneal epithelial cells), Bowman's layer (also known as the anterior limiting membrane), Corneal stroma (also substantia propria), Descemet's membrane (also posterior limiting membrane), and Corneal endothelium (simple squamous or low cuboidal monolayer, approximately 5 μm thick, of mitochondria-rich cells).

As used herein, the phrase "decreased or low-level production/release/delivery/excretion of hyaluronic acid from and/or in the cornea" means a concentration of hyaluronic acid which is less than the concentration of hyaluronic acid in the tears of a normal (i.e., non-diseased) person, or, in certain embodiments, less than 25 (or about 25) nanograms per milligram of proteins, as determined using the method described in Dreyfuss J L, Regatieri C V, Coelho B, et al. Altered hyaluronic acid content in tear fluid of patients with adenoviral conjunctivitis. An Acad Bras Cienc. 2015; 87(1): 455-462. That method (the Dreyfuss Method) is reproduced below:
Sample Collection
For collecting the tears, Schirmer strips were placed in the temporal side of each eye under the eyelid, during 5 minutes, without any use of topical anesthetics. The strips were dried at room temperature and stored at −20° C. until analysis.
Tear Sample Preparation
Tear compounds were eluted from the Schirmer strips using 100 μL of distilled water, and hyaluronic acid and protein content analyses were performed.
Hyaluronic Acid Measurement
Hyaluronic acid content in tear fluids was assayed by a non-isotopic fluoroassay (See Martins Jr, Passerotti C C, Maciel R M, Sampaio Lo, Dietrich C P and Nader H B. 2003.) Practical determination of hyaluronan by a new noncompetitive fluorescence-based assay on serum of normal and cirrhotic patients. Anal Biochem 319: 65-72.) Eluted tear fluids and standard concentrations of hyaluronic acid (Sigma, St. Louis, Mo.) were added to 96 multiwell plates (FluoroNUNC Maxisorp-microtiterplates, Roskilde, Denmark) previously coated with hyaluronic acid-binding protein. The plates were then sequentially incubated with biotinylated hyaluronic acid-binding protein and europiumlabeled streptavidin (Amershan, Piscataway, N.J.). Afterwards, the europium remaining in the solid phase was released by an enhancement solution and the fluorescence was measured using a time-resolved flurometer (Perkin- Elmer Life Sciences-Wallac Oy, Turku, Finland). The data (counts/s) were processed automatically using the MultiCalc software program (Perkin-Elmer Life Sciences-Wallac Oy) and values are expressed as ng/mg protein.

Protein Analysis

Total tear protein concentration was determined using a colorimetric assay kit according to the manufacturer's instructions (Protein Assay Kit from Bio-Rad, Hercules, Calif.). The protein profile was analyzed through sodium dodecylsulfate polyacrylamide gel electrophoresis (SDS-PAGE) as previously described (See Laemmli UK. 1970. Cleavage of structural proteins during the assembly of the head of bacteriophage T4. Nature 227: 680-685). Briefly, 10 μg of protein from the tear samples were applied to a 3-20% linear gradient polyacrylamide gel under reducing conditions. After electrophoresis, the gels were stained by comassie blue (Bio-Rad, Hercules, Calif.). Each protein band was quantified by densitometry using the software ImageJ Version 10.2 for Mac (U.S. National Institutes of Health, Bethesda, Md., USA). The results are expressed by arbitrary densitometric units (ADU).

As used herein, the phrase "decreased or low-level production/release/delivery/excretion of mucin from and/or in the cornea" means a concentration of MUC5AC which is less than the concentration of MUC5AC in the tears of a normal (i.e., non-diseased) person, or, in certain embodiments, less than 6, optionally less than 8, nanograms per milligram of proteins, as determined using the method described in Uchino Y, Uchino M, Yokoi N, et al. Alteration of Tear Mucin 5AC in Office Workers Using Visual Display Terminals: The Osaka Study. *JAMA Ophthalmol.* n2014; 132(8):985-992. That method (the Uchino Method) is reproduced below:

MUC5AC Concentration in Tears

The concentration of the secreted mucin MUC5AC in the tear samples was quantified by enzyme-linked immunoassay (E90756Hu; USCN Life Science). (See Maker A V, Katabi N, Gonen M, et al. Pancreatic cyst fluid and serum mucin levels predict dysplasia in intraductal papillary mucinous neoplasms of the pancreas. *Ann Surg Oncol.* 2011; 18(1):199-206.) All samples were analyzed according to the manufacturer's guidelines. Absorbance was measured at 450 nm, and the standard solutions in the kit were recombinant human MUC5AC. A protein assay reagent kit (BCA Protein Assay Kit; Pierce) was used to determine the protein concentration in the tear samples. The MUC5AC concentration was normalized to the tear protein content and expressed as MUC5AC protein (nanograms) per tear total protein (milligrams).

As used herein, a composition that is "essentially free" of an ingredient means the composition that has about 2% or less of that ingredient by weight based on the total weight of the composition. Preferably, a composition that is essentially free of an ingredient has about 1% or less, more preferably about 0.5% or less, more preferably about 0.1% or less, more preferably about 0.05 or less, more preferably about 0.01% or less by weight based on the total weight of composition of the ingredient. In certain more preferred embodiments, a composition that is essentially free of an ingredient is free of the ingredient, i.e. has none of that ingredient in the composition.

As used herein, "microemulsion" means emulsions possessing one or more of the following characteristics: i) they are formed spontaneously or substantially spontaneously when their components are brought into contact, that is without substantial energy supply, e.g. in the absence of heating or the use of high shear equipment or other substantial agitation; ii) they exhibit thermodynamic stability; iii) they are monophasic; iv) they are substantially non-opaque, i.e. are transparent or opalescent when viewed by optical microscopic means; and/or v) in their undisturbed state, they are optically isotropic, though an anisotropic structure may be observable using e.g. x-ray technique. The particles of a microemulsion may be spherical, though other structures are feasible, e.g. liquid crystals with lamellar, hexagonal or isotropic symmetries. Generally, micro-emulsions comprise droplets or particles having a maximum dimension (e.g. diameter) of less than 1,500 Å, preferably less than 1000 Å, preferably less than 500 Å, but greater than 100 Å. Included within this definition of microemulsion are self-emulsifying drug delivery systems (SEDDS). SEDDS are isotropic mixtures of oil, surfactant (with or without co-surfactant) and co-solvent which spontaneously emulsify when exposed to an aqueous medium with gentle agitation. SEDDS may be used to improve bioavailability of poorly water soluble drugs via oral administration. The addition of a co-solvent facilitate the formation of a self-emulsifying system as it significantly reduces the interfacial tension. In so doing, it creates a fluid interfacial film with sufficient flexibility to take up different curvatures required to form microemulsion over a wide range of compositions. Further detail regarding SEDDS can be found in US Pat. Publication US2018/0036233A1 to Shabaik et al., herein incorporated by reference in its entirety.

As used herein, "ophthalmologically acceptable" means that the ingredients which the term describes are suitable for use in contact with tissues (e.g., the soft tissues of the eye or periorbital skin tissues) without undue toxicity, incompatibility, instability, irritation, allergic response, and the like. As will be recognized by one of skill in the art, ophthalmologically acceptable salts are acidic/anionic or basic/cationic salts.

As used herein, the term "safe and effective amount" means an amount of disclosed the extract, compound or of the composition sufficient to induce, promote and/or improve the production/release/delivery/excretion of hyaluronic acid and/or mucin from and/or in one or more layer of the cornea, but low enough to avoid serious side effects. The safe and effective amount of the compound, extract, or composition will vary with e.g. the age, health and environmental exposure of the end user, the duration and nature of the treatment, the specific extract, ingredient, or composition employed, the particular pharmaceutically-acceptable carrier utilized, and like factors.

The term "retinol-like properties and/or benefits" means the properties and/or benefits induced by retinol.

In certain embodiments, the present invention as disclosed herein may be practiced in the absence of any compound or element (or group of compounds or elements) which is not specifically disclosed herein.

In general, IUPAC nomenclature rules are used herein and according to the following term definitions.

The term "C1-8 alkyl," whether used alone or as part of a substituent group, refers to a saturated aliphatic branched or straight-chain monovalent hydrocarbon radical having from 1-8 carbon atoms. For example, "C1-8 alkyl" specifically includes the radicals methyl, ethyl, 1-propyl, 2-propyl, 1-butyl, 2-butyl, tert-butyl, 1-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Said term may also refer to the corresponding alkyldiyl radical. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{1-4}$alkyl," whether used alone or as part of a substituent group, refers to a saturated aliphatic branched or straight-chain monovalent hydrocarbon radical or alkyldiyl linking group having a specified number of carbon atoms, wherein the radical is derived by the removal of one hydrogen atom from a carbon atom and the alkyldiyl linking group is derived by the removal of one hydrogen atom from each of two carbon atoms in the chain. The term "$C_{1-4}$alkyl" refers to a radical having from 1-4 carbon atoms in a linear or branched arrangement. For example, "$C_{1-4}$alkyl" specifically includes the radicals methyl, ethyl, 1-propyl, 2-propyl, 1-butyl, 2-butyl, tert-butyl, 1-butyl, and the like. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{2-4}$alkenyl" refers to an alkenyl radical having from 2-4 carbon atoms. For example, specifically includes the radicals ethenyl, propenyl, allyl (2-propenyl), butenyl and the like. As described above, an alkenyl radical may be similarly attached to a core molecule and further substituted where indicated.

The term "halo" as such or in combination with other terms means halogen atom, such as fluoro, chloro, bromo or iodo.

The term "substituted," refers to a core molecule in which one or more hydrogen atoms have been replaced with that amount of substituents allowed by available valences. Substitution is not limited to the core molecule, but may also occur on a substituent radical, whereby the radical becomes a linking group.

The term "independently selected" refers to two or more substituents that may be selected from a substituent variable group, wherein the selected substituents may be the same or different.

The term "dependently selected" refers to one or more substituent variables that are specified in an indicated combination for substitution in a core molecule (e.g. variables that refer to groups of substituents appearing in a tabular list of compounds).

Acceptable salts from inorganic bases include, for example, sodium or potassium salts, and the like. Acceptable salts from organic bases include, for example, salts formed with primary, secondary, or tertiary amines, and the like.

Compounds/Extracts Exhibiting Retinol-Like Properties and/or Benefits

The present invention comprises compounds and/or extracts having retinol-like properties and/or benefits for use in treating dry eye including, selected from or selected from the group consisting of one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

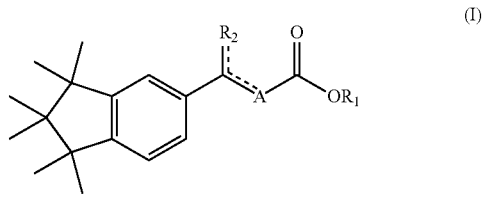

wherein—
the dotted lines represent simple or double bound; optionally one of the dotted line is a double bound;
$R_1$ represent an H, a carbonated chain, linear, cyclic, or branched, saturated or unsaturated, comprising from 1 to 20 carbon atoms;
$R_2$ represent a carbonated chain, linear, cyclic ringed, or branched, saturated or unsaturated, comprising from 1 to 20 carbon atoms; optionally a methyl (—$CH_3$) or methylene (=$CH_2$) moiety; a carbonated chain, linear, ringed, or branched, saturated or unsaturated, comprising from 1 to 20 carbon atoms; optionally from 1 to 10 carbon atoms; optionally 6 carbon atoms; optionally an aromatic moiety, optionally a phenyl moiety; optionally 2-methyl-prop-1,3-diene.

*Acronychia, Licaria, Calendula* and/or *Trigonella* Botanical Plant Extract(s)

In certain embodiments, the compounds/extracts exhibiting retinol-like properties and/or benefits are, or comprise, extracts, or sources of extracts, of plant *Acronychia, Licaria, Calendula* and/or *Trigonella*. The *Acronychia, Licaria, Calendula* or *Trigonella* extracts, or sources of such extracts, are obtained from plants of the genus *Acronychia, Licaria, Calendula* or *Trigonella*.

Plants of the genus *Acronychia*, from which extracts useful in the present invention are, obtained include, for example, *Acronychia aberrans, Acronychia acidula* (also referred herein as lemon aspen), *Acronychia acronychioides, Acronychia acuminate, Acronychia baeuerlenii, Acronychia chooreechillum, Acronychia crassipetala, Acronychia eungellensis, Acronychia imperforate, Acronychia laevis, Acronychia laurifolia, Acronychia littoralis, Acronychia oblongifolia, Acronychia octandra, Acronychia parviflora, Acronychia pauciflora, Acronychia pedunculata, Acronychia pubescens, Acronychia* species (Batavia Downs), *Acronychia suberosa, Acronychia vestita, Acronychia wilcoxiana*, and combinations of two or more thereof. In one embodiment, the extract used in the present invention dis obtained from *Acronychia acidula*.

Plants of the genus *Licaria*, from which extracts useful in the present invention are obtained, include, for example, *Licaria vernicosa, Licaria brittoniana, Licaria canella, Licaria cubensis, Licaria velutina* and *Licaria triandra*, and combinations of two or more thereof. There are about 40 species of genus *Licaria* reported and are endemic to Central and South Americas. In one embodiment, the extract used in the present invention is obtained from *Licaria vernicosa*.

There are about 15-20 species of genus *Calendula* reported and are found in southwestern Asia, western Europe, Macaronesia, and the Mediterranean. Plants of the genus *Calendula*, from which extracts useful in the present invention are obtained, include, for example, *Calendula arvensis* (field marigold); *Calendula maderensis* (Madeiran marigold); and *Calendula officinalis* (pot marigold) and combinations of two or more thereof. In one embodiment, the extract used in the present invention is obtained from *Calendula officinalis*.

Plants of the genus *Trigonella* include 36 known species Plants of the genus *Trigonella*, from which extracts useful in the present invention are obtained, include, for example, *Trigonella foenum-graecum, Trigonella balansae, Trigonella corniculata, Trigonella maritima, Trigonella spicata, Trigonella caerulea, Trigonella occulta, Trigonella polycerata, Trigonella Calliceras, Trigonella Cretica* and combinations of two or more thereof. *Trigonella foenum-graecum* or herb fenugreek is the best-known member of the genus *Trigonella*. In one embodiment, the extract used in the present invention is obtained from *Trigonella foenum-graecum*.

In certain embodiments, the extract used in the present invention is a mixture of extracts obtained from plants of the genus *Acronychia, Licaria, Calendula* and/or *Trigonella*.

Extracts of *Licaria vernicosa* useful in the present invention can be obtained from the Baruch S. Blumerg Institute, Doylestown, Pa. (formerly known as IVHR). In certain embodiments, one extract comes from the woody part of the plant (E2) and the second extract was from the roots of the plant (E3). Within the nomenclature of IHVR collection, the two extracts are labeled as IHVR_40256_G10=X-005348-001E002 and as IHVR_40256_E10=X-005346-001M002 respectively. The woody parts and the roots of *Licaria vernicosa* (Mez) Kosterm. can be collected from Guyana. 504.3 g of dried, ground woody plant material can be extracted with an ample methanol, which can be dried under vacuum to afford 10.54 g of crude methanol extract (E2) for X-005348-001E002. 403.8 g of dried, ground root material can be extracted with ample methanol, which can be dried under vacuum to afford 18.11 g of crude methanol extract (E3) for X-005346-001M002.

In certain embodiments, the *Acronychia* and/or *Licaria* extracts useful in the present invention comprise compounds having the Formula II:

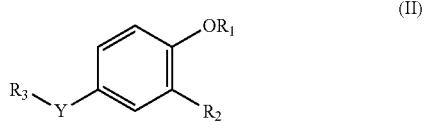

(II)

wherein:
$R_1$ is selected from the group consisting of $C_1$-$C_{20}$ alkyl, $C_2$-$C_{20}$ alkenyl, $C_2$-$C_{20}$ alkynyl, and $C_3$-$C_8$ cycloalkyl or aryl;
$R_2$ is selected from the group consisting of hydrogen, hydroxyl, $C_1$-$C_6$ alkyl, $C_2$-$C_6$ alkenyl, $C_2$-$C_6$ alkynyl, $C_3$-$C_8$ cycloalkyl or aryl, —$OC_1$-$C_6$ alkyl, —$OC_2$-$C_6$ alkenyl, —$OC_2$-$C_6$ alkynyl, —$OC_3$-$C_8$ cycloalkyl or aryl, thiol, —$SC_1$-$C_6$alkyl, —$SC_2$-$C_6$ alkenyl, —$SC_2$-$C_6$ alkynyl, —$SC_3$-$C_8$ cycloalkyl or aryl, —$NR_4C_1$-$C_6$ alkyl, —$NR_4C_2$-$C_6$ alkenyl, —$NR_4C_2$-$C_6$ alkynyl, and —$NR_4C_3$-$C_8$cycloalkyl or aryl;
$R_3$ is selected from —$CO_2H$, —$CO_2R_4$ or an isosteric equivalent of a carboxy group, wherein
$R_4$ is $C_1$-$C_6$ alkyl, $C_2$-$C_6$ alkenyl, $C_3$-$C_8$ cycloalkyl or aryl; and
Y is —($CH_2$—$CH_2$)—, —(CH=CH)—, or —(C≡C)—;
or a ophthalmologically acceptable salt thereof.

In certain embodiments, the *Acronychia* and/or *Licaria* extracts useful in the present invention comprises compounds having the Formula II:

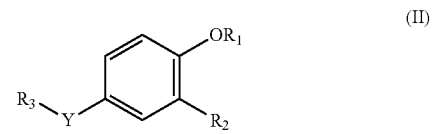

(II)

wherein:
$R_1$ is selected from the group consisting of $C_5$-$C_{16}$ alkyl, $C_5$-$C_{16}$ alkenyl, and $C_5$-$C_{16}$ alkynyl, more preferably $C_5$-$C_{16}$ alkenyl, including, for example, farnesyl;
$R_2$ is selected from the group consisting of hydrogen, hydroxyl, —$OC_1$-$C_6$alkyl, —$OC_2$-$C_6$ alkenyl, —$OC_2$-$C_6$ alkynyl, —$OC_3$-$C_8$ cycloalkyl, more preferably hydrogen, hydroxyl, —$OC_1$-$C_6$ alkyl, even more preferably hydrogen or —$OC_1$-$C_3$ alkyl;
$R_3$ is selected from —$CO_2H$, —$CO_2R_4$ wherein $R_4$ is $C_1$-$C_6$ alkyl, or an isosteric equivalent of a carboxy group; and
Y is —($CH_2$—$CH_2$)— or —(CH=CH)—;
or a ophthalmologically-acceptable salt thereof.

In certain embodiments, at least one of the compounds of Formula II is present in the extract the *Acronychia* and/or *Licaria* at a concentration equal to or greater than 1% (or about 1%) to about 20%, or optionally from about 7% (or about 7%) to about 10% (or about 10%), by weight of the *Acronychia* and/or *Licaria* extract.

In certain embodiments, the compounds of Formula II useful in the present invention are in the form of an acid or alkylester selected from (or, selected from the group consisting of) 3-(4-farnesyloxyphenyl)-propionic acid, 3-(4-farnesyloxy-3-hydroxyphenyl)-propionic acid, 3-(4-farnesyloxy-3-methoxyphenyl)-propionic acid, alkylesters thereof, in particular ethyl esters thereof, and combinations of two or more thereof.

In certain embodiments, the compound of Formula II useful in the present invention is 3-(4-farnesyloxyphenyl)-propionic acid and/or its ethyl ester.

In certain embodiments, the compound of Formula II useful in the present invention is 3-(4-farnesyloxy-3-hydroxyphenyl)-propionic acid and/or its ethyl ester.

In certain embodiments, the compound of Formula II useful in the present invention is 3-(4-farnesyloxy-3-methoxyphenyl)-propionic acid and/or its ethyl ester.

Compounds and extracts derived from *Acronychia* species are described in U.S. Pat. No. 9,220,928, which patent is herein incorporated by reference in entirety.

In certain embodiments, the 3-(4-farnesyloxyphenyl)-propionic acid and/or its ethyl ester is present in the extract the *Acronychia* and/or *Licaria* at a concentration equal to or greater than 1% (or about 1%) to about 20%, or optionally from about 7% (or about 7%) to about 10% (or about 10%), by weight of the *Acronychia* and/or *Licaria* extract.

Any of a variety of extracts of *Acronychia* and/or *Licaria* may be used for embodiments where the method comprises applying such an extract. The extract may be obtained from any part of the plant such as the fruit, the seed, the bark, the leaf, the flower, the roots and the wood.

In certain embodiments, the extract is obtained from the fruit of the plant. Suitable extracts of *Acronychia* or *Licaria* fruit, seed, bark, leaves, flower, root, and wood may be obtained using conventional methods including, but not limited to, direct extraction of material from the biomass by grinding, macerating, pressing, squeezing, mashing, centrifuging, and/or processes such as cold percolation, agitation/distillation, microwave assisted extraction, supercritical/subcritical $CO_2$ compressed gas extraction with or without polar modifiers, pressurized solvent extraction, accelerated solvent extraction, pressurized or normal hot water extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like. Any of a variety of solvents including polar solvents, non-polar solvents, or combinations of two or more thereof may be used in methods of comprising solvent extraction.

Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids.

In one embodiment, the extract comprises an extract of *Acronychia acidula*. In another embodiment, the extract of the invention comprises a combination of polar and non-polar extracts of from *Acronychia acidula* fruit. In another embodiment, the extract of the invention comprises alcoholic or glycolic extracts of *Acronychia acidula* fruit.

In one embodiment, the extract comprises an extract of *Licaria vernicosa*. In another embodiment, the extract of the invention comprises a combination of polar and non-polar extracts of from *Licaria vernicosa* wood or *Licaria vernicosa* root. In another embodiment, the extract of the invention comprises alcoholic extracts of *Licaria vernicosa* wood or *Licaria vernicosa* root.

In another embodiment, the extract of the invention comprises a polar extract prepared by extracting from fruit of *Acronychia acidula*, wood of *Licaria vernicosa*, or root of *Licaria vernicosa* using a polar solvent comprising water, $C_1$-$C_8$ alcohols, $C_1$-$C_8$ polyols, $C_1$-$C_8$ glycols, and combinations of two or more thereof. In certain embodiments, the extract is extracted using one or more $C_1$-$C_4$ alcohols, $C_1$-$C_4$ polyols, and/or $C_1$-$C_4$ glycols. In certain embodiments, the extract is prepared using a solvent comprising methanol, ethanol, or a combination thereof with or without presence of water. In another embodiment, the extract is a polar extract extracted from *Acronychia acidula* fruit using a combination of alcohol and water. In yet another embodiment, the extract is a polar extract extracted from the ground wood of *Licaria vernicosa*, or ground root of *Licaria vernicosa* using methanol.

In yet another embodiment, the extract comprises a non-polar extract prepared by extracting from *Acronychia acidula* fruit, *Licaria vernicosa* wood, or *Licaria vernicosa* root using a non-polar solvent comprising one or more $C_1$-$C_8$ alkanes, $C_1$-$C_8$ cycloalkanes, $C_1$-$C_8$ alkyl ethers, $C_1$-$C_8$ alkyl esters and/or chloroform, more preferably one or more $C_1$-$C_8$ alkanes, $C_1$-$C_8$ alkyl esters and/or chloroform. In yet another embodiment, the non-polar extract is extracted from *Acronychia acidula* fruit, *Licaria vernicosa* wood, or *Licaria vernicosa* root using hexanes, ethyl acetate, chloroform or mixtures of two or more thereof. In yet another embodiment, the non-polar extract is extracted from *Acronychia acidula* fruit using ethyl acetate.

In one embodiment, the extract comprises an extract of *Calendula officinalis*. In another embodiment, the extract of the invention comprises a combination of polar and non-polar extracts of *Calendula officinalis* petals. In another embodiment, the extract of the invention comprises a non-polar extract of *Calendula officinalis* petals.

In one embodiment, the extract comprises an extract of *Trigonella foenum-graecum*. In another embodiment, the extract of the invention comprises a combination of polar and non-polar extracts of *Trigonella foenum-graecum* leaves. In another embodiment, the extract of the invention comprises a non-polar extract of *Trigonella foenum-graecum* leaves.

In yet another embodiment, the *Calendula* and/or *Trigonella* extract is a non-polar extract prepared using a non-polar solvent comprising one or more $C_1$-$C_8$ alkanes, $C_1$-$C_8$ cycloalkanes, $C_1$-$C_8$ alkyl ethers, $C_1$-$C_8$ alkyl esters and/or chloroform, more preferably one or more $C_1$-$C_8$ alkanes, $C_1$-$C_8$ alkyl esters and/or chloroform.

In yet another embodiment, *Calendula* and/or *Trigonella* extract is a non-polar extract prepared using hexanes, ethyl acetate, chloroform, or mixtures of two or more thereof. In yet another embodiment, the extract is a non-polar extract prepared using ethyl acetate.

In one embodiment, the botanical extracts may be obtained via extraction of cell cultures of various plants, including cell cultures of the genera *Acronychia*, *Licaria*, *Calendula*, or *Trigonella*. The cell cultures which are extracted to obtain botanical extracts for use in the invention may be of any form including suspension cell cultures and the like.

Extracts of *Calendula officinalis* and of *Trigonella foenum-graecum* can be obtained from Caithness Biotechnologies Ltd, UK (http://www.caithnessbiotechnologies.com/). These extracts are part of The Phytotitre Natural Product Library available to everyone for purchase. Alternatively, the extracts can be obtained using a preparation method described by Caithness Biotechnologies Ltd. as non-polar and prepared with a mixture of methanol and methylene chloride. For detailed description please consult webpage http://caithnessbiotechnologies.com/contact.html. In a typical extraction, a preweighed dried powdered biomass is suspended and stirred in a mixture of methanol/methylene chloride (1:1) over night at ambient temperature. The suspension is then filtered, filtrate is dried under reduced pressure to a residue free of solvents.

In certain embodiments, the extract of the *Acronychia*, *Licaria*, *Calendula*, and/or *Trigonella* is present in the compositions of the present invention in an amount of from about 0.001% to about 10%, optionally, from about 0.001% to about 5%, or, optionally, from about 0.01% to about 1%, by weight of the composition.

Bacterial Extract(s) of the Genus *Actinomyces* Exhibiting Retinol-Like Properties and/or Benefits In certain embodiments, the compounds/extracts exhibiting retinol-like properties and/or benefits are, or comprise bacterial extract(s) of the genus *Actinomyces*. Bacteria of the genus *Actinomyces* include many species fully characterized, as well as some of them which are not well characterized, for example one species collected from USA and labeled as species A5640. A sample of this bacteria is collected, grown in culture and made into an extract. The extract is a part of natural products collection now in control of the Baruch S. Blumerg Institute, Doylestown, Pa. (formerly known as the Institute of Hepatitis Virus Research Labs (IHVR)). Within the nomenclature of IHVR collection, the extract is labeled as IHVR_39565_F7.

In one embodiment, the extract used in the present invention is obtained from *Actinomyces* species with a capacity to produce similar chemical composition as is produced by extract A5640. In another embodiment, the bacteria are collected in the USA and the strain is identical to previously assigned species A5640.

In certain embodiments, the extract of *Actinomyces* is present in the composition of the present invention in an amount of from about 0.001% to about 10%, optionally, from a about 0.001% to about 5%, or, optionally, from about 0.01% to about 1%, by weight of the composition.

Compound(s) of Formula (I) Exhibiting Retinol-Like Properties and/or Benefits.

In certain embodiments, the compounds/extracts exhibiting retinol-like properties and/or benefits are, or comprise the compounds of Formula (I).

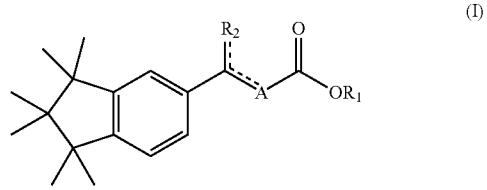

(I)

wherein—
    the dotted lines represent simple or double bound; optionally one of the dotted line is a double bound;
    $R_1$ represent an H, a carbonated chain, linear, cyclic, or branched, saturated or unsaturated, comprising from 1 to 20 carbon atoms;
    $R_2$ represent a carbonated chain, linear, cyclic ringed, or branched, saturated or unsaturated, comprising from 1 to 20 carbon atoms; optionally a methyl (—$CH_3$) or methylene (=$CH_2$) moiety; a carbonated chain, linear, ringed, or branched, saturated or unsaturated, comprising from 1 to 20 carbon atoms; optionally from 1 to 10 carbon atoms; optionally 6 carbon atoms; optionally an aromatic moiety, optionally a phenyl moiety; preferably 2-methyl-prop-1,3-diene.

In certain embodiments, the compounds of Formula (I) include the corresponding salts of such metal ions as, but not limited to, $Li^+$, $Na^+$, $K^+$, $Ca^{2+}$, or $Mg^{2+}$.

In certain embodiments, the compounds of Formula I are:

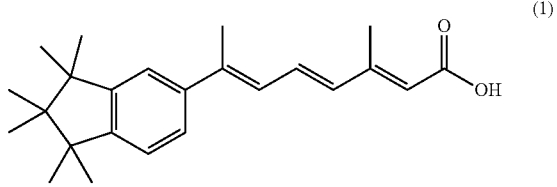 [SMILES: CC(/C=C/C=C(\C)c1ccc2c(c1)C(C)(C)C(C)(C)C2(C)C)=C\C(=O)O]

(1)

(2E,4E,6E)-7-(1,1,2,2,3,3-hexamethyl-2,3-dihydro-1H-inden-5-yl)-3-methylocta-2,4,6-trienoic acid or

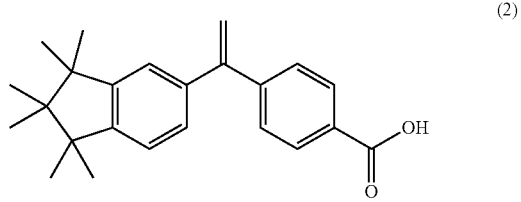 [SMILES: C=C(c1ccc(C(=O)O)cc1)c1ccc2c(c1)C(C)(C)C(C)(C)C2(C)C]

(2)

4-(1-(1,1,2,2,3,3-hexamethyl-2,3-dihydro-1H-inden-5-yl) vinyl)benzoic acid and, in each case, their derivatives that display retinoid-like activity. These compounds are referred referenced in Examples 8 and 9 below as Compound 1 and Compound 2, respectively The present invention is directed to compounds of Formula I such as (2E,4E,6E)-7-(1,1,2,2,3,3-hexamethyl-2,3-dihydro-1H-inden-5-yl)-3-methylocta-2,4,6-trienoic acid and 4-(1-(1,1,2,2,3,3-hexamethyl-2,3-dihydro-1H-inden-5-yl)vinyl)benzoic acid and their derivatives that display retinoid-like activity and mixtures thereof.

Mixtures of any of the above the compounds/extracts/extract sources exhibiting retinol-like properties and/or benefits may also be used.

Compounds and extracts of Formula I are described in US Patent Publication 2019/0091122, which patent is herein incorporated by reference in entirety.

In certain embodiments, the compound(s) of Formula I is present in the composition of the present invention in an amount of from about 0.0001% to about 20%, optionally, from about 0.001% to about 10%, optionally, from about 0.01% to about 5%, or optionally from about 0.2 to about 2%, by weight of the composition. In yet another embodiment, the compound(s) of Formula I is present in the composition of the present invention in an amount of from about 0.0001 to about 1%, optionally from about 0.001 to about 1%, or optionally from about 0.01 to about 1%, by weight of the composition.

Compositions The present inventors have discovered that compounds and/or extracts having retinol-like properties and/or benefits can promote and/or improve delivery/excretion of hyaluronic acid from corneal epithelial cells.

Permeation Enhancer

In certain embodiments, the compositions of the present invention optionally comprise a permeation enhancer.

Suitable permeation enhancers include (selected from or selected from the group consisting of) either alone or in combination, surfactants such as saponins, polyoxyethylene, polyoxyethylene ethers of fatty acids such as polyoxyethylene 4-, 9-, 10-, and 23-lauryl ether, polyoxyethylene 10- and 20-cetyl ether, polyoxyethylene 10- and 20-stearyl ether, sorbitan monooleate, sorbitan monolaurate, polyoxyethylene monolaurate, polyoxyethylene sorbitans such as polyoxyethylene sorbitan monolaurate, decamethonium, decamethonium bromide, and dodecyltrimethylammonium bromide; chelators such natural polyacids (e.g., citric acid), phosphate salts (e.g., disodium pyrophosphate), phosphonates, bisphosphonates (e.g., etridronic acid), aminocarboxylic acids (e.g., ethylenediaminetetraacetic acid (EDTA) and disodium EDTA) and ethylenediamine-N,N'-disuccinic acid (EDDS)); bile salts and acids such as cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, and urosdeoxycholic acid; fusidic acid derivatives, glycyrrhizic acid, and ammonium glycyrrhizide, with saponin EDTA, fusidic acid, polyoxyethylene 9-lauryl ether, polyoxyethylene 20-stearylether, glycocholate, or mixtures of any of the above.

The concentration of permeation enhancer administered should be the minimum amount needed to sufficiently increase absorption of the compound and/or extract through the mucous or other barrier membranes of the eye. Generally, concentrations ranging from 0.01% (or about 0.01%), optionally, from 0.05% (or about 0.05%), optionally, from 0.1% (or about 0.1%), optionally, from 0.15% (or about 0.15%), optionally, from 0.2% (or about 0.2%), optionally, from 0.25% (or about 0.25%) to 2% (or about 2%), optionally, to 2.5% (or about 2.5%), optionally, to 3% (or about 3%), optionally, to 3.5%, (or about 3.5%), optionally, to 4% (or about 4%), optionally, to 4.5% (or about 4.5%), optionally, to 5% (or about 5%), optionally, to 5.5% (or about 5.5%), optionally, to 6% (or about 6%), optionally, to 6.5% (or about 6.5%), optionally, to 7% (or about 7%), optionally, to 7.5% (or about 7.5%), optionally, to 8% (or about 8%), optionally, to 8.5% (or about 8.5%), optionally, to 9% (or about 9%), optionally, to 9.5% (or about 9.5%), optionally, to 10% (or about 10%), optionally, to 10.5% (or about 10.5%), optionally, to 11% (or about 11%), optionally, to 11.5% (or about 11.5%), optionally, to 12% (or about 12%), optionally, to 12.5% (or about 12.5%), optionally, to 13% (or about 13%), optionally, to 13.5% (or about 13.5%), optionally, to 14% (or about 14%), optionally, to 14.5% (or about 14.5%), optionally, to 15% (or about 15%), optionally, to 15.5% (or about 15.5%), optionally, to 16% (or about 16%), optionally, to 16.5% (or about 16.5%), optionally, to 17% (or about 17%), optionally, to 17.5% (or about 17.5%), optionally, to 18% (or about 18%), optionally, to 18.5% (or about 18.5%), optionally, to 19% (or about 19%), optionally, to 19.5% (or about 19.5%), optionally, to 20% (or about 20%), of the total composition (w/v), are useful in the compositions of the present invention.

Ophthalmologically Acceptable Carrier

The compositions of the present invention also comprise an aqueous, oil-in-water emulsion, water-in-oil emulsion carrier, oil-in-water microemulsion, or water-in-oil microemulsion carrier. The carrier is ophthalmologically acceptable. Useful oil-in-water and water-oil-carriers can be found in US Patent Publication 20030165545A1 and U.S. Pat. Nos. 9,480,645, 8,828,412 and 8,496,976, each of which patent documents are herein incorporated by reference in its entirety.

In certain embodiments, the compositions of the present invention include emulsions, optionally, self-emulsifying emulsions, including an oily component, such as one or more oils, for example, and without limitation, mineral oil and/or one or more other conventional well known and/or commercially available oils suitable for use in the present invention; a surfactant component which includes three or more surfactants; and an aqueous component which includes an aqueous phase. In addition, a number of additional components may be included in the present compositions. The compositions of the present invention are substantially non-toxic and/or non-irritating and/or non-damaging to the eye and can provide a protective function for ocular cells and tissues.

One or more oils or oily substances are used to form the present compositions. Any suitable oil or oily substance or combinations of oils or oily substances may be employed provided such oils and/or oily substances are effective in the present compositions, and do not cause any substantial or significant detrimental effect to the human or animal to whom the composition is administered, or to the contact lens being treated, or the wearing of the treated contact lens, or to the wearer of the treated contact lens. The oily component may, for example, and without limitation, be a higher fatty acid glyceride, for example, castor oil, corn oil, sunflower oil and the like and mixtures thereof. The oily component may include one or more non-polar oils such as mineral oil, silicone oil and the like and mixtures thereof.

The ophthalmologically acceptable carrier (or, compositions of the present invention) may optionally comprise one or more additional excipients and/or one or more additional active ingredients. Examples of such optional components are described below.

Excipients commonly used in ophthalmic compositions include, but are not limited to, demulcents, tonicity agents, preservatives, chelating agents, buffering agents (other than and in addition to the organic acids of the present invention), and surfactants. Other excipients comprise solubilizing agents, stabilizing agents, comfort-enhancing agents, polymers, emollients, pH-adjusting agents (other than and in addition to the organic acids of the present invention), and/or lubricants. Any of a variety of excipients may be used in the compositions of the present invention including water, mixtures of water and water-miscible solvents, such as vegetable oils or mineral oils comprising from 0.5% to 5% non-toxic water-soluble polymers, natural products, such as agar and acacia, starch derivatives, such as starch acetate and hydroxypropyl starch, and also other synthetic products such as polyvinyl alcohol, polyvinylpyrrolidone, polyvinyl methyl ether, polyethylene oxide, and preferably cross-linked polyacrylic acid and mixtures thereof.

Demulcents or soothing agents used with embodiments of the present invention include, but are not limited to, cellulose derivatives (such hydroxyethyl cellulose, methyl cellulose, hypromellose or mixtures thereof), hyaluronic acid or salt thereof (such as sodium hyaluronate), tamarind seed extract, glycerin, polyvinyl pyrrolidone, polyethylene oxide, polyethylene glycol, propylene glycol and polyacrylic acid and mixtures thereof. In certain embodiments, one or more of hyaluronic acid, propylene glycol, tamarind seed extract, glycerin and/or polyethylene glycol 400 are the demulcents or soothing agents. In certain embodiments, the demulcent or soothing agent is selected from hyaluronic acid, tamarind seed extract or mixtures thereof.

Compositions of the present invention are ophthalmologically suitable for application to a subject's eyes. The term "aqueous" typically denotes an aqueous formulation wherein the excipient is >about 50%, more preferably >about 75% and in particular >about 90% by weight water. In certain embodiments, the compositions of the present invention are essentially free of compounds which irritate the eye. In certain embodiments, the compositions of the present invention are essentially free of free fatty acids and $C_1$ to $C_4$ alcohols. In certain embodiments, the compositions of the present invention are comprise less than 40% (or about 40%), optionally, less than 35% (or about 35%), optionally, less than 30% (or about 30%), optionally less than 25% (or about 25%), optionally, less than 20% (or about 20%), optionally, less than 15% (or about 15%), optionally less than 10% (or about 10%), or optionally, less than 5% (or about 5%), by weight of the total composition, of a non-alcohol, organic excipient or solvent. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the composition as it is delivered, such devices being known in the art.

In certain embodiments, the compositions of the present invention are isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The compositions of the present invention generally have an osmolality in the range of 220-320 mOsm/kg, or, optionally, have an osmolality in the range of 235-300 mOsm/kg. The ophthalmic compositions will generally be formulated as sterile aqueous solutions.

The osmolality of the compositions of the present invention may be adjusted with tonicity agents to a value which is compatible with the intended use of the compositions. For example, the osmolality of the composition may be adjusted to approximate the osmotic pressure of normal tear fluid, which is equivalent to about 0.9 w/v % of sodium chloride in water. Examples of suitable tonicity adjusting agents include, without limitation, sodium, potassium, calcium and magnesium chloride; dextrose; glycerin; propylene glycol; mannitol; sorbitol and the like and mixtures thereof. In one embodiment, a combination of sodium chloride and potassium chloride are used to adjust the tonicity of the composition.

The compositions of the present invention can also be used to administer pharmaceutically active compounds. Such compounds include, but are not limited to, glaucoma therapeutics, pain relievers, anti-inflammatory and anti-allergy medications, and anti-microbials. More specific examples of pharmaceutically active compounds include betaxolol, timolol, pilocarpine, carbonic anhydrase inhibitors and prostglandins; dopaminergic antagonists; post-surgical antihypertensive agents, such as para-amino clonidine (apraclonidine); anti-infectives such as ciprofloxacin, moxifloxacin, and tobramycin; non-steroidal and steroidal anti-inflammatories, such as naproxen, diclofenac, nepafenac, suprofen, ketorolac, tetrahydrocortisol and dexamethasone; dry eye therapeutics such as PDE4 inhibitors; and anti-allergy medications such as H1/H4 inhibitors, H4 inhibitors, olopatadine or mixtures thereof.

It is also contemplated that the concentrations of the ingredients comprising the formulations of the present invention can vary. A person of ordinary skill in the art would understand that the concentrations can vary depending on the addition, substitution, and/or subtraction of ingredients in a given formulation.

In certain embodiments, the compositions of the present invention may have a pH which is compatible with the intended use, and is often in the range of 4 (or about 4) to 10 (or about 10), optionally between 6 (or about 6) to 8 (to about 8), optionally between 6.5 (or about 6.5) to 7.5 (or about 7.5), or optionally between 6.8 (or about 6.8) to 7.2 (or about 7.2).

In certain embodiments, a variety of conventional buffers may be employed, such as phosphate, borate, citrate, acetate, histidine, tris, bis-tris and the like and mixtures thereof. Borate buffers include boric acid and its salts, such as sodium or potassium borate. Potassium tetraborate or potassium metaborate, which produce boric acid or a salt of boric acid in solution, may also be employed. Hydrated salts such as sodium borate decahydrate can also be used. Phosphate buffers include phosphoric acid and its salts; for example, $M_2HPO_4$ and $MH_2PO_4$, wherein M is an alkali metal such as sodium and potassium. Hydrated salts can also be used. In one embodiment of the present invention, $Na_2HPO_4 \cdot 7H_2O$ and $NaH_2PO_2 \cdot H_2O$ are used as buffers. The term phosphate also includes compounds that produce phosphoric acid or a salt of phosphoric acid in solution. Additionally, organic counter-ions for the above buffers may also be employed. The concentration of buffer generally varies from about 0.01 to 2.5 w/v % and more preferably varies from about 0.05 to about 0.5 w/v %.

In certain embodiments, the viscosity of the compositions of the present invention range from about 1 to about 500 cps, optionally from about 10 to about 200 cps, or optionally from about 10 to about 100 cps, when measured using a TA Instrument AR 2000 rheometer. The TA Instrument AR 2000 rheometer should be used with the AR2000 flow test method of the TA Rheological Advantage software with a 40 mm steel plate geometry; the viscosity ranges should be obtained by measuring steady state flow controlling shear rate from 0 $sec^{-1}$ to 200 $sec^{-1}$.

In certain embodiments, the compositions of the present invention are useful as, and in the form of, eye-drop solution, eye wash solution, contact lens lubricating and/or rewetting solution, spray, mist or any other manner of administering a composition to the eye.

The compositions of the present invention may also be useful as, and in the form of, packing solutions for contact lenses. In certain embodiments, as packing solutions, the compositions of the present invention may be sealed in blister packaging and, also, suitable for undergoing sterilization.

Examples of blister packages and sterilization techniques are disclosed in the following references which are hereby incorporated by reference in their entirety, U.S. Pat. Nos. D435,966; 4,691,820; 5,467,868; 5,704,468; 5,823,327; 6,050,398, 5,696,686; 6,018,931; 5,577,367; and 5,488,815. This portion of the manufacturing process presents another method of treating the ophthalmic devices with anti-allergic agent, namely adding anti-allergic agents to a solution prior to sealing the package, and subsequently sterilizing the package. This is the preferred method of treating ophthalmic devices with anti-allergic agents.

Sterilization can take place at different temperatures and periods of time. The preferred sterilization conditions range from about 100° C. for about 8 hours to about 150° C. for about 0.5 minute. More preferred sterilization conditions range from about 115° C. for about 2.5 hours to about 130° C. for about 5.0 minutes. The most preferred sterilization conditions are about 124° C. for about 18 minutes.

When used as packing solutions, the compositions of the present invention may be water-based solutions. Typical packing solutions include, without limitation, saline solutions, other buffered solutions, and deionized water. In certain embodiments, the packing solution is an aqueous solution of deioinized water or saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. In certain embodiments, the pH of the packing solution is as described above. The buffered solutions may additionally include 2-(N-morpholino)ethanesulfonic acid (MES), sodium hydroxide, 2,2-bis(hydroxymethyl)-2,2',2''-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution or deionized water. The particularly preferred solution contains about 500 ppm to about 18,500 ppm sodium borate, most particularly preferred about 1000 ppm of sodium borate.

If any ingredients incorporated into the packing solutions are subject to oxidative degradation, agents that stabilize packing solutions containing such ingredients may be added. Such "oxidative stabilization agents" include but are not limited to chelants such as EDTA, Dequest, Desferal, silica, chitin derivatives such as chitosan, cellulose and its derivatives, and N,N,N',N',N'',N''-hexa(2-pyridyl)-1,3,5-tris(aminomethyl)benzene, and certain macrocyclic ligands such as crown ethers, ligand containing knots and catenands. See, David A. Leigh et al Angew. Chem Int. Ed., 2001, 40, No. 8, pgs. 1538-1542 and Jean-Claude Chambron et al. Pure & Appl. Chem., 1990, Vol. 62, No. 6, pgs. 1027-1034. Oxidative stabilization agents may include other compounds that inhibit oxidations such as those selected from the group consisting of 2,2',2'',6,6',6''-Hexa-(1,1-dimethylethyl)4,4', 4''-[(2,4,6-trimethyl-1,3,5-benzenetriyl)-trismethylene]-triphenol (Irganox 1330), 1,3,5tris[3,5-di(1,1-dimethylethyl)4-hydroxybenzyl]-1H,3H,5H-1,3,5-triazine-2,4,6-trione, pentaerythrityl tetrakis[3-[3,5-di(1,1-dimethylethyl)-4-hydroxyphenyl]-propionate], octadecyl-3-[3,5-di(1,1-dimethylethyl)-4-hydroxyphenyl]-propionate, tris[2,4-di(1,1-dimethylethyl)-phenyl]-phosphite, 2,2'-di(octadecyloxy)-5,5'-spirobi(1,3,2-dioxaphosphorinane), dioctadecyl disulphide, didodecyl-3,3'-thiodipropionate, dioctadecyl-3,3'-thiodipropionate, butylhydroxytoluene, ethylene bis[3,3-di[3-(1,1-dimethylethyl)-4-hydroxyphenyl]butyrate] and mixtures thereof. The preferred oxidative stabilization agents are diethylenetriaminepentaacetic acid ("DTPA"), or salts of DTPA such as CaNa3DTPA, ZnNa3DTPA, and Ca2DTPA. See, U.S. App. Pat. No. 60/783,557 filed on, Mar. 17, 2006, entitled "Methods for Stabilizing Oxidatively Unstable Pharmaceutical Compositions" and its corresponding non-provisional filing which are hereby incorporated by reference in their entirety. In certain embodiments, the concentration of oxidative stabilization agents in the solution be from about 2.5 µmoles/liter to about, 5000 µmoles/liter, optionally, from about 20 µmoles/liter to about 1000 µmoles/liter, optionally from about 100 µmoles/liter to about 1000 µmoles/liter, or optionally from about 100 µmoles/liter to about 500 µmoles/liter.

In particular embodiments, the compositions of the present invention are formulated for administration at any frequency of administration, including once a week, once every five days, once every three days, once every two days, twice a day, three times a day, four times a day, five times a day, six times a day, eight times a day, every hour, or greater frequency. Such dosing frequency is also maintained for a varying duration of time depending on the therapeutic needs of the user. The duration of a particular therapeutic regimen may vary from one-time dosing to a regimen that extends for months or years. One of ordinary skill in the art would be familiar with determining a therapeutic regimen for a specific indication.

The composition and products containing such compositions of this invention may be prepared using methodology that is well known by an artisan of ordinary skill.

EXAMPLES

Any compositions of the present invention as described in following examples illustrate specific embodiments of compositions of the present invention, but are not intended to be limiting thereof. Other modifications can be undertaken by the skilled artisan without departing from the spirit and scope of this invention.

The following test methods were used in the Examples:

Example 1

Compositions of Lemon aspen extract showed an increase of MUC1, MUC4 and MUC16 gene expressions in human epicorneal 3D tissues when treated in the medium.

EpiCorneal 3D human tissues were purchased from MatTek Company (Ashland, Mass., USA). Upon receiving, epicorneal 3D human tissues, they were incubated in MatTek assay medium overnight following the manufacturer's instruction. The epicorneal 3D human tissues were divided into three treatment groups with at least three tissues per group. Lemon aspen extract were added, respectively, into the culture medium containing the human epicorneal tissues of two of the treatment groups to produce media concentrations of 0.001% or 0.01% (w/v), respectively. The epicorneal tissues in all four treatment groups were allowed to incubate for two days. The extract of lemon aspen used in the and extracted and supplied by Southern Cross Botanicals (Knockrow Nsw, Australia). After the two days' incubation, gene expressions of mucin 1 (MUC1), mucin 4 (MUC4) and mucin 16 (MUC16) were analyzed. After two days' incubation, the human epicorneal 3D tissues were cut in halves and half of the tissues were lysed in 350 µL lysis buffer, consisting of 100 parts RLT buffer (RNeasy Mini kit, Qiagen, Valencia, Calif.), to one part 2-mercaptoethanol. RNA was extracted from the solutions using the RNeasy Mini Kit (Qiagen, Valencia, Calif.) according to manufacturer's instructions and RNA was eluted in 25 µL RNase-free water.

Reverse transcription (RT) was performed using the Applied Biosystems High Capacity Reverse Transcription Kit (ThermoFisher Scientific, Bridgewater, N.J.). Gene expression assays sold under the tradename TAQMAN for mucin-1 (MUC1), mucin-4 (MUC4) and mucin-16 (MUC16) polymerase (RNA) II polypeptide A (POLR2A), and Master Mix were purchased from ThermoFisher Scientific (Bridgewater, N.J.). qPCR analysis was performed using TaqMan® Master Mix (ThermoFisher Scientific, Bridgewater, N.J.), and run on a real time PCR system sold under the tradename QUANTSTUDIO 7 Flex System (ThermoFisher Scientific, Bridgewater, N.J.). The expression of the MUC1, MUC4 and MUC16 genes were normalized against the expression of the human POLR2A housekeeping gene. The fold changes were calculated in comparison to the untreated control (UT) and two-tailed two-sample Student t-tests (Microsoft Office Excel 2007; Microsoft, Redmond, Wash., USA) were performed. Results are shown in FIG. 1.

Example 2

Compositions of Lemon aspen extract showed an increase of mucin-1 secretion in human epicorneal 3D tissues when treated in the medium.

Figure 2:
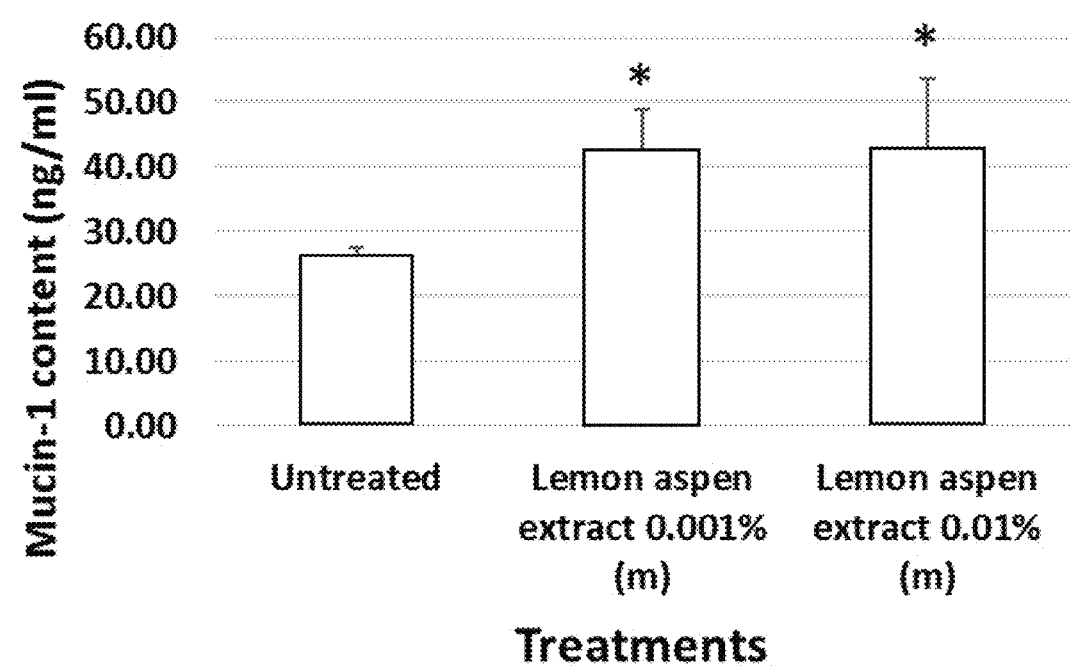
FIG. 2 depicts bar graphs showing lemon aspen extract induced Mucin-1 secretion in corneal epithelial cells.

EpiCorneal 3D human tissues were purchased from MatTek Company (Ashland, Mass., USA). Upon receiving, epicorneal 3D human tissues, they were incubated in MatTek assay medium overnight following the manufacturer's instruction. The epicorneal 3D human tissues were divided into three treatment groups with at least three tissues per group. Lemon aspen extract were added, respectively, into the culture medium containing the human epicorneal tissues of two of the treatment groups to produce media concentrations of 0.001% or 0.01% (w/v), respectively. The epicorneal tissues in all four treatment groups were allowed to incubate for two days. After the two days, culture media were collected for measuring mucin 1 secretion using human mucin-1 (CA15-3) enzyme-linked immunosorbent assay (ELISA) kit (EHMUC1, ThermoFisher Scientific, Bridgewater, N.J.) following the manufacturer's protocol. To assess activity, the colorimetric change was measured using a microplate reader (SpectraMax M2E, Molecular Devices, Sunnyvale, Calif., USA). This assay employs the standard enzyme-linked immunoassay technique, so there is a linear correlation between Mucin-1 concentration in the sample and the colorimetric change. A standard curve was generated, with the Mucin-1 concentration on the x-axis and absorbance on the y-axis to indicate corresponding Mucin-1 concentration. Results are shown below in FIG. 2.

Example 3

An extract of lemon aspen (Acronychia acidula) showed an increase of HAS3 gene expression induction in human epicorneal 3D tissues when applied topically.

EpiCorneal 3D human tissues were purchased from MatTek Company (Ashland, Mass., USA). Upon receiving the epicorneal 3D human tissues, they were incubated in MatTek assay medium overnight following the manufacturer's instruction. The epicorneal 3D human tissues were divided into two treatment groups with at least three tissues per group. A solution of lemon aspen extract (0.1% w/v extract in a 30/70 (v/v) polypropylene glycol/ethanol vehicle) was topically applied to the human epicorneal tissues of one of the treatment groups. The epicorneal tissues in both treatment groups were allowed to incubate for two days. After the two days, gene expression of hyaluronic acid synthase 3 (HAS3) was analyzed. HAS3 is the enzyme involved in the synthesis of hyaluronic acid. The extract of lemon aspen used in the and extracted and supplied by Southern Cross Botanicals (Knockrow Nsw, Australia). After two days' incubation, the human epicorneal 3D tissues were cut in halves and half of the tissues were lysed in 350 µL lysis buffer, consisting of 100 parts RLT buffer (RNeasy Mini kit, Qiagen, Valencia, Calif.), to one part 2-mercaptoethanol. RNA was extracted from the solutions using the RNeasy Mini Kit (Qiagen, Valencia, Calif.) according to manufacturer's instructions and RNA was eluted in 25 µL RNase-free water.

Figure 3:
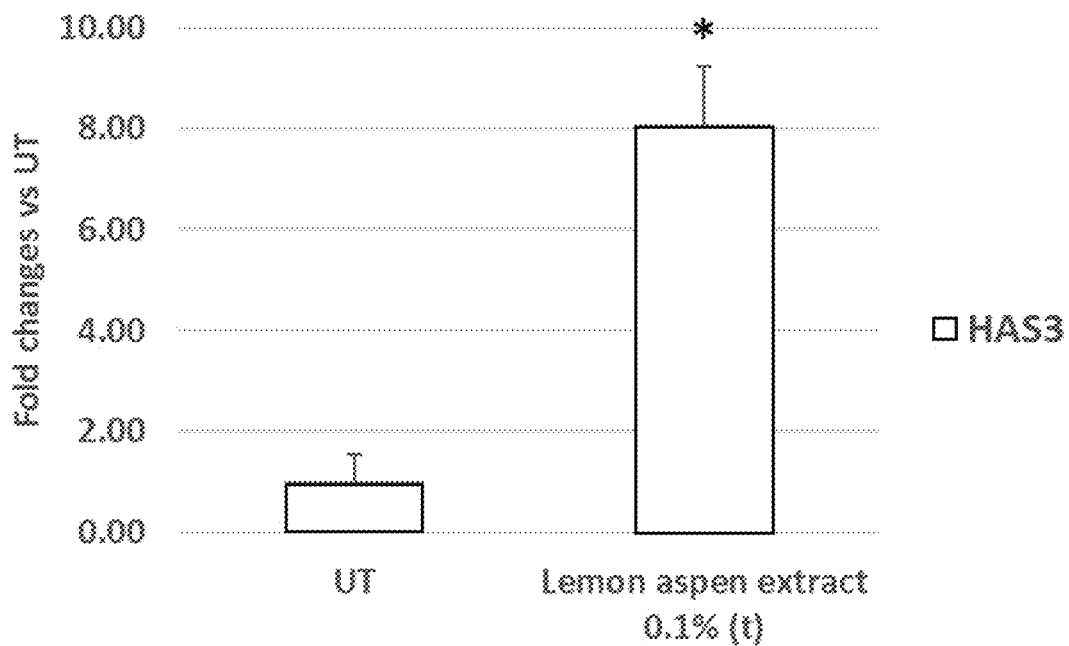
FIG. 3 depicts bar graphs showing lemon aspen extract induced HAS3 gene expression in corneal epithelial cells.

Reverse transcription (RT) was performed using the Applied Biosystems High Capacity Reverse Transcription Kit (ThermoFisher Scientific, Bridgewater, N.J.). Gene expression assays sold under the tradename TAQMAN for hyaluronic acid synthase 3 (HAS3), polymerase (RNA) II polypeptide A (POLR2A), and Master Mix were purchased from ThermoFisher Scientific (Bridgewater, N.J.). qPCR analysis was performed using TaqMan® Master Mix (ThermoFisher Scientific, Bridgewater, N.J.), and run on a real time PCR system sold under the tradename QUANTSTUDIO 7 Flex System (ThermoFisher Scientific, Bridgewater, N.J.). The expression of the HAS3 gene was normalized against the expression of the human POLR2A housekeeping gene. The fold changes were calculated in comparison to the untreated control (UT) and two-tailed two-sample Student t-tests (Microsoft Office Excel 2007; Microsoft, Redmond, Wash., USA) were performed. Results were shown in FIG. 3.

Example 4

Extract of lemon aspen showed an increase of hyaluronic acid bioactivity in human epicorneal 3D tissues when applied topically.

Figure 4:
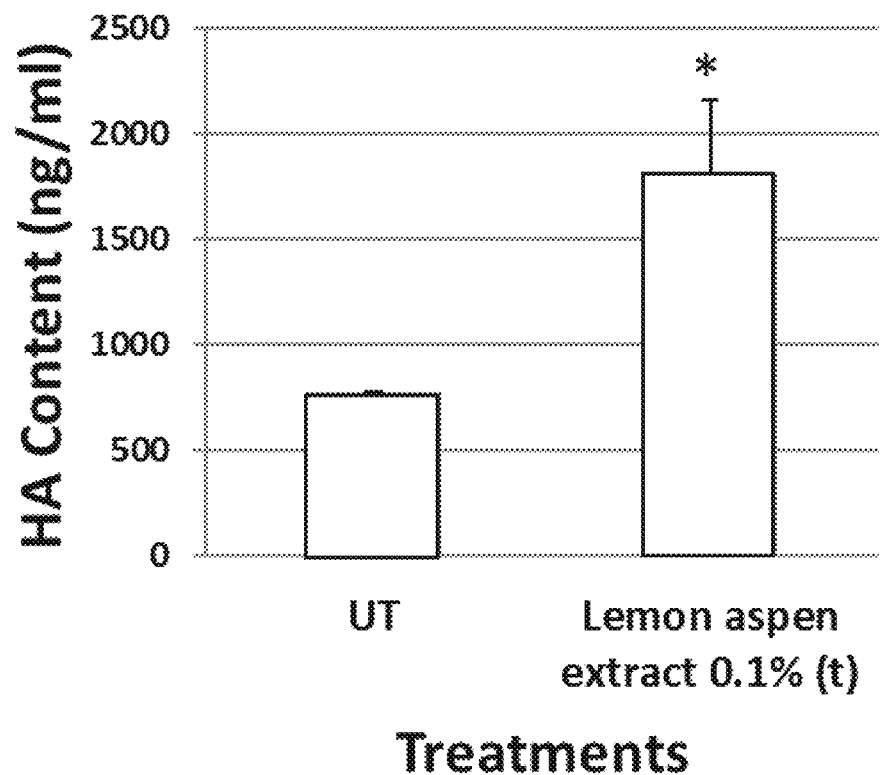
FIG. 4 depicts bar graphs showing lemon aspen extract induced HA secretion in corneal epithelial cells.

EpiCorneal 3D human tissues were purchased from MatTek Company (Ashland, Mass., USA). Upon receiving the epicorneal 3D human tissues, they were incubated in MatTek assay medium overnight following the manufacturer's instruction. The epicorneal 3D human tissues were divided into two treatment groups with at least three tissues per group. A solution of lemon aspen extract (0.1% w/v extract in a 30/70 (v/v) polypropylene glycol/ethanol vehicle) was topically applied to human epicorneal tissues of one of the treatment groups. The epicorneal tissues in both treatment groups were allowed to incubate for two days. After the two days, the culture media were collected for measuring hyaluronic acid (HA) secretion using HA enzyme-linked immunosorbent assay (ELISA) kit (K-1200, Echelon, Salt Lake City, Utah, USA) following the manufacturer's protocol. The extract of lemon aspen used in this Example 4 is the same as the extract of lemon aspen used in Example 3. To assess activity, the colorimetric change was measured at 405 nm using a microplate reader (SpectraMax M2E, Molecular Devices, Sunnyvale, Calif., USA). This assay employs the competitive enzyme-linked immunosorbent assay technique, so there is an inverse correlation between HA concentration in the sample and the colorimetric change. A standard curve was generated, with the HA concentration on the x-axis and absorbance on the y-axis to indicate corresponding HA concentration. Results were shown in FIG. 4.

Example 5

Lemon aspen extract showed an increase of HAS3 gene expression induction in human epicorneal 3D tissues when treated in the medium.

EpiCorneal 3D human tissues were purchased from MatTek Company (Ashland, Mass., USA). Upon receiving the epicorneal 3D human tissues, they were incubated in MatTek assay medium overnight following the manufacturer's instruction. The epicorneal 3D human tissues were divided into four treatment groups with at least three tissues per group. Lemon aspen extract were added, respectively, into the culture medium containing the human epicorneal tissues of three of the treatment groups to produce media concentrations of 0.0001%, 0.001% or 0.01% (w/v), respectively. The epicorneal tissues in all four treatment groups were allowed to incubate for two days. The extract of lemon aspen used in this Example 5 is extracted and supplied by Southern Cross Botanicals (Knockrow Nsw, Australia), but using a different extraction process than that used to extract the extract used in Example 3. After the two days' incubation, gene expression of hyaluronic acid synthase 3 (HAS3) was analyzed as described below. The human epicorneal 3D tissues were cut in halves and half of the tissues were lysed in 350 µL lysis buffer, consisting of 100 parts RLT buffer (RNeasy Mini kit, Qiagen, Valencia, Calif.), to one part 2-mercaptoethanol. RNA was extracted from the solutions using the RNeasy Mini Kit (Qiagen, Valencia, Calif.) according to manufacturer's instructions and RNA was eluted in 25 µL RNase-free water.

Figure 5:
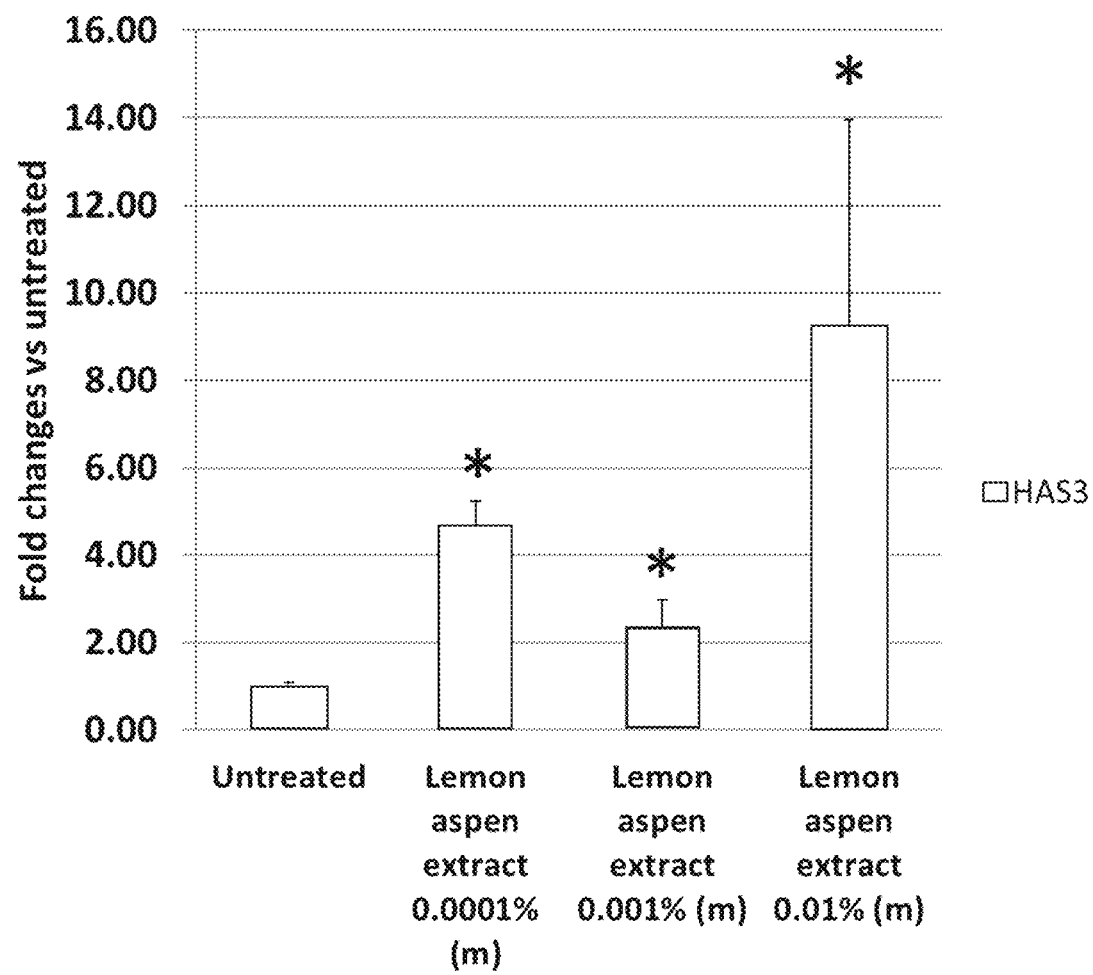
FIG. 5 depicts bar graphs showing lemon aspen extract induced HAS3 gene expression in corneal epithelial cells.

Reverse transcription (RT) was performed using the Applied Biosystems High Capacity Reverse Transcription Kit (ThermoFisher Scientific, Bridgewater, N.J.). Gene expression assays sold under the tradename TAQMAN for hyaluronic acid synthase 3 (HAS3), polymerase (RNA) II polypeptide A (POLR2A), and Master Mix were purchased from ThermoFisher Scientific (Bridgewater, N.J.). qPCR analysis was performed using TaqMan® Master Mix (ThermoFisher Scientific, Bridgewater, N.J.), and run on a real time PCR system sold under the tradename QUANTSTUDIO 7 Flex System (ThermoFisher Scientific, Bridgewater, N.J.). The expression of the HAS3 gene was normalized against the expression of the human POLR2A housekeeping gene. The fold changes were calculated in comparison to the untreated control (UT) and two-tailed two-sample Student t-tests (Microsoft Office Excel 2007; Microsoft, Redmond, Wash., USA) were performed. Results were shown in FIG. 5.

Example 6

Lemon aspen extract showed an increase of hyaluronic acid bioactivity in human epicorneal 3D tissues when treated in the medium.

Figure 6:
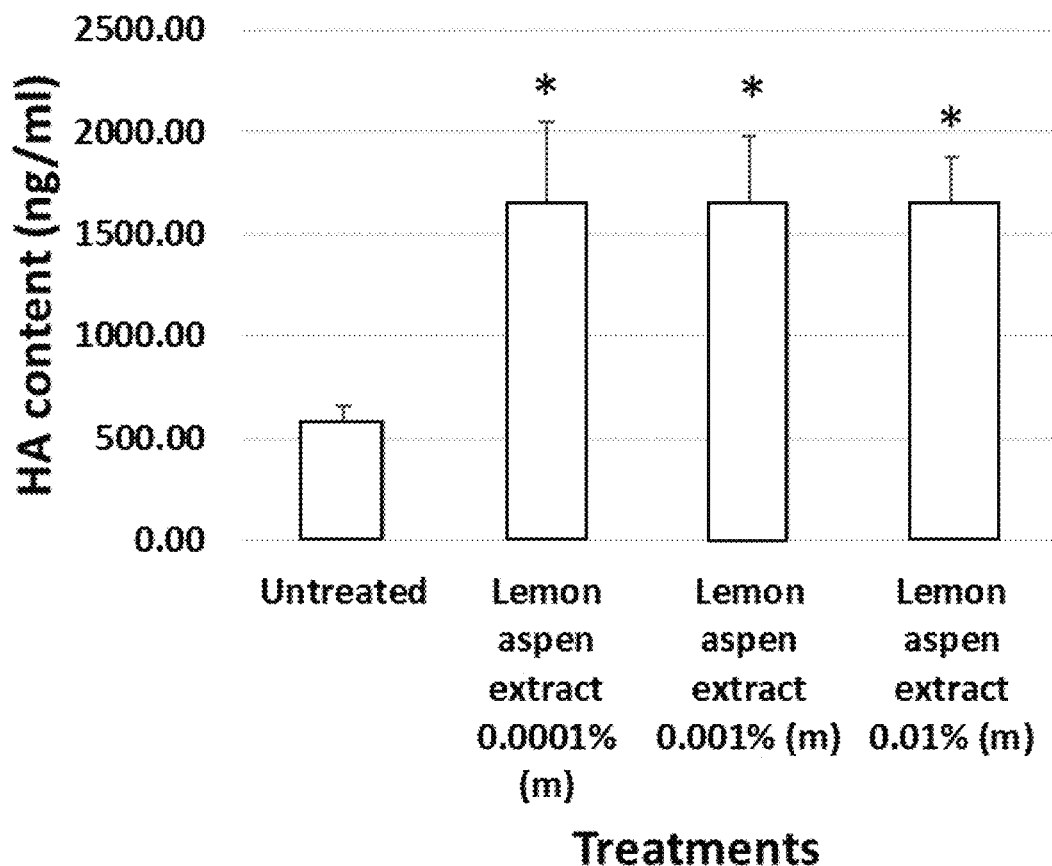
FIG. 6 depicts bar graphs showing lemon aspen extract induced HA secretion in corneal epithelial cells.

EpiCorneal 3D human tissues were purchased from Mat-Tek Company (Ashland, Mass., USA). Upon receiving the epicorneal 3D human tissues, they were incubated in Mat-Tek assay medium overnight following the manufacturer's instruction. The epicorneal 3D human tissues were divided into four treatment groups with at least three tissues per group. Lemon aspen extract were added, respectively, into the culture medium containing the human epicorneal tissues of three of the treatment groups to produce media concentrations of 0.0001%, 0.001% or 0.01% (w/v), respectively. The epicorneal tissues in all four treatment groups were allowed to incubate for two days. The extract of lemon aspen used in this Example 6 is the same as the extract of lemon aspen used in Example 5. After the two days, the culture media were collected for measuring hyaluronic acid (HA) secretion using HA enzyme-linked immunosorbent assay (ELISA) kit (K-1200, Echelon, Salt Lake City, Utah, USA) following the manufacturer's protocol. To assess activity, the colorimetric change was measured using a microplate reader (SpectraMax M2E, Molecular Devices, Sunnyvale, Calif., USA. This assay employs the competitive enzyme-linked immunosorbent assay technique, so there is an inverse correlation between HA concentration in the sample and the colorimetric change. A standard curve was generated, with the HA concentration on the x-axis and absorbance on the y-axis to indicate corresponding HA concentration. Results were shown in FIG. 6.

Example 7

Table 1 illustrates the components of such formulations (as illustrated in formulations 7A-7D), which components can be incorporated as described below using conventional mixing technology.

TABLE 1

| INGREDIENT | 7A Useful for Relief of Dry Eye Irritation | | 7B Useful for Relief of Dry Eye Irritation | | 7C Useful for Relief of Dry Eye Irritation for Contact Lenses | | 7D Useful for Relief of Dry Eye Irritation for Contact Lenses | |
|---|---|---|---|---|---|---|---|---|
| | % w/w | amount per batch (gms) | % w/w | amount per batch (gms) | % w/w | amount per batch (gms) | % w/w | amount per batch (gms) |
| Sodium Hyaluronate | 0.20 | 2.0 | 0.30 | 3.0 | 0.15 | 1.5 | 0.15 | 1.5 |
| Lemon Aspen Extract | 0.10 | 1.0 | 0.01 | 0.10 | 0.10 | 1.0 | 0.01 | 0.10 |
| Polysorbate 80 | 1.0 | 10.0 | 0.2 | 2.0 | 1.0 | 10.0 | 0.2 | 2.0 |
| Polysorbate 20 | 5.0 | 50.0 | 1.0 | 10.0 | 2.0 | 20.0 | 1.0 | 10.0 |
| Polyethylene Glycol 400 | 0.25 | 2.5 | 0.25 | 2.5 | 0 | 0 | 0 | 0 |
| Boric Acid | 0.60 | 6.0 | 0.60 | 6.0 | 0.60 | 6.0 | 0.60 | 6.0 |
| Sodium Borate | 0.05 | 0.50 | 0.05 | 0.50 | 0.05 | 0.50 | 0.05 | 0.50 |
| Sodium Chloride* | | | | | | | | |
| Potassium Chloride | 0.10 | 1.0 | 0.10 | 1.0 | 0.10 | 1.0 | 0.10 | 1.0 |
| Calcium Chloride Dihydrate | 0.006 | 0.06 | 0.006 | 0.06 | 0.006 | 0.06 | 0.006 | 0.06 |
| Magnesium Chloride | 0.006 | 0.06 | 0.006 | 0.06 | 0.006 | 0.06 | 0.006 | 0.06 |
| Sodium Chlorite Dihydrate | 0.014 | 0.14 | 0.014 | 0.14 | 0.014 | 0.14 | 0.014 | 0.14 |
| Polyquaternium 42 (33% aqueous) | 0.0015 | 0.015 | 0.0015 | 0.015 | 0.0015 | 0.015 | 0.0015 | 0.015 |
| Sodium Chlorite Dihydrate | 0.014 | 0.14 | 0.014 | 0.14 | 0.014 | 0.14 | 0.014 | 0.14 |
| 1N Sodium Hydroxide solution** | | | | | | | | |
| 1N Hydrochloric Acid solution** | | | | | | | | |
| Purified Water*** | | | | | | | | |
| Total | 100.00% | 1000.0 g | 100.00% | 1000.0 g | 100.00% | 1000.00 g | 100.00% | 1000.00 g |

*can be adjusted to tonicity of 280-290 mOsm/Kg
**can adjust to pH 7.2
***optionally, q.s to 100% w/w For Examples 7A-7D: The Sodium Hyaluronate can be supplied by CONTIPRO A.S. (DOLNI, DOBROUC, CZECH REPUBLIC)

For Examples 7A-7D: The Lemon Aspen Extract (Abacross™ *Acronychia acidula* fruit extract) can be supplied by SOUTHERN CROSS BOTANICALS (KNOCKROW NSW, AUSTRALIA).

For Examples 7A-7D: The Polysorbate 20 can be supplied by Merck KGaA (DARMSTADT, GERMANY).

For Examples 7A-7D: The Polysorbate 80 can be supplied by Merck KGaA (DARMSTADT, GERMANY).

For Examples 7A-7B: The Polyethylene Glycol 400 can be supplied by Clariant Produkte (BURGKIRCHEN, GERMANY).

For Examples 7A-7D: The Boric Acid can be supplied by Merck KGaA (DARMSTADT, GERMANY).

For Examples 7A-7D: The Sodium Borate can be supplied by Merck KGaA (DARMSTADT, GERMANY).

For Examples 7A-7D: The Sodium Chloride can be supplied by Caldic (DUSSELDORF, GERMANY).

For Examples 7A-7D: The Potassium Chloride can be supplied by Merck KGaA (DARMSTADT, GERMANY).

For Examples 7A-7D: The Calcium Chloride Dihydrate can be supplied by Merck KGaA (DARMSTADT, GERMANY).

For Examples 7A-7D: The Magnesium Chloride can be supplied by KGaA (DARMSTADT, GERMANY).

For Examples 7A-7D: The Polyquaternium-42 (33% aqueous) can be supplied by DSM BIOMEDICAL (BERKELEY, Calif., USA).

For Examples 7A-7D: The Sodium Chlorite Dihydrate can be supplied by Oxychem (WICHITA, Kans., USA)

For Examples 7A-7D: The 1N Sodium Hydroxide can be supplied by VWR (RADNER, Pa., USA).

For Examples 7A-7D: The 1N Hydrochloric acid can be supplied by VWR (RADNER, Pa., USA).

Solution 7A can be prepared as follows:
1. To a 1500 ml beaker is added 800 grams of Purified Water USP.
2. To the above is added 10 g of Polysorbate 80 and 50 g of Polysorbate 20. The solution is mixed until both are fully mixed and dissolved.
3. To the above is added 1.0 g of Lemon Aspen Extract. The solution is mixed until the Lemon Aspen Extract is dissolved.
4. The solution is filtered through a 0.45 micron filter and returned to a 1500 ml beaker.
5. To the solution of Step 4 is added 2.0 grams of Sodium Hyaluronate. The solution is mixed to fully dissolve the Sodium Hyaluronate.
6. The following ingredients are next added sequentially, allowing for each to dissolve before adding the next: 2.5 grams Polyethylene Glycol 400, 6.0 grams Boric acid, 0.05 gram Sodium Borate, 1.0 gram Potassium Chloride, 0.06 gram Calcium Chloride Dihydrate, 0.06 gram Magnesium Chloride, and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Solution 7B can be prepared as follows:
1. To a 1500 ml beaker is added 800 grams of Purified Water USP.
2. To the above is added 2 g of Polysorbate 80 and 10 g of Polysorbate 20. The solution is mixed until both are fully mixed and dissolved.
3. To the above is added 0.1 g of Lemon Aspen Extract. The solution is mixed until the Lemon Aspen Extract is dissolved.
4. The solution is filtered through a 0.45 micron filter and returned to a 1500 ml beaker.
5. To the solution of Step 4 is added 3.0 grams of Sodium Hyaluronate. The solution is mixed to fully dissolve the Sodium Hyaluronate.
6. The following ingredients are next added sequentially, allowing for each to dissolve before adding the next: 2.5 grams Polyethylene Glycol 400, 6.0 grams Boric acid, 0.05 gram Sodium Borate, 1.0 gram Potassium Chloride, 0.06 gram Calcium Chloride Dihydrate, 0.06 gram Magnesium Chloride, and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Solution 7C can be prepared as follows:
1. To a 1500 ml beaker is added 800 grams of Purified Water USP.
2. To the above is added 10 g of Polysorbate 80 and 20 g of Polysorbate 20. The solution is mixed until both are fully mixed and dissolved.
3. To the above is added 1.0 g of Lemon Aspen Extract. The solution is mixed until the Lemon Aspen Extract is dissolved.
4. The solution is filtered through a 0.45 micron filter and returned to a 1500 ml beaker.
5. To the solution of Step 4 is added 1.5 grams of Sodium Hyaluronate. The solution is mixed to fully dissolve the Sodium Hyaluronate.
6. The following ingredients are next added sequentially, allowing for each to dissolve before adding the next: 6.0 grams Boric acid, 0.05 gram Sodium Borate, 1.0 gram Potassium Chloride, 0.06 gram Calcium Chloride Dihydrate, 0.06 gram Magnesium Chloride and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Solution 7D can be prepared as follows:
1. To a 1500 ml beaker is added 800 grams of Purified Water USP.
2. To the above is added 2 g of Polysorbate 10 and 50 g of Polysorbate 20. The solution is mixed until both are fully mixed and dissolved.
3. To the above is added 0.1 g of Lemon Aspen Extract. The solution is mixed until the Lemon Aspen Extract is dissolved.

4. The solution is filtered through a 0.45 micron filter and returned to a 1500 ml beaker.
5. To the solution of Step 4 is added 1.5 grams of Sodium Hyaluronate. The solution is mixed to fully dissolve the Sodium Hyaluronate.
6. The following ingredients are next added sequentially, allowing for each to dissolve before adding the next: 6.0 grams Boric acid, 0.05 gram Sodium Borate, 1.0 gram Potassium Chloride, 0.06 gram Calcium Chloride Dihydrate, 0.06 gram Magnesium Chloride and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Example 8

Table 2 illustrates the components of formulations of the present invention (as illustrated in formulations 8A-8D), which components can be incorporated as described below using conventional mixing technology.

TABLE 2

| INGREDIENT | 8A Useful for Relief of Dry Eye Irritation | | 8B Useful for Relief of Dry Eye Irritation for Contact Lenses | | 8C Useful for Relief of Dry Eye Irritation for Contact Lenses | | 8D Useful for Relief of Dry Eye Irritation | |
|---|---|---|---|---|---|---|---|---|
| | % w/w | amount per batch (gms) | % w/w | amount per batch (gms) | % w/w | amount per batch (gms) | % w/w | amount per batch (gms) |
| Sodium Hyaluronate | 0 | 0 | 0 | 0 | 0.120 | 1.20 | 0.120 | 1.20 |
| Tamarind Seed Polysaccharide | 0 | 0 | 0 | 0 | 0.200 | 2.00 | 0.200 | 2.00 |
| Lemon Aspen Extract | 0.10 | 1.0 | 0.10 | 1.0 | 0.01 | 0.10 | 0.01 | 0.10 |
| Polysorbate 80 | 1.0 | 10.0 | 1.0 | 10.0 | 0.2 | 2.0 | 0.2 | 2.0 |
| Polysorbate 20 | 5.0 | 50.0 | 5.0 | 50.0 | 1.0 | 10.0 | 1.0 | 10.0 |
| Polyethylene Glycol 400 | 0 | 0 | 0 | 0 | 0.25 | 2.5 | 0.25 | 2.5 |
| Glycerin | 0.25 | 2.5 | 0.25 | 2.5 | 0.25 | 2.5 | 0.25 | 2.5 |
| Hypromellose E3 2910 | 0.198 | 1.98 | 0.198 | 1.98 | 0.198 | 1.98 | 0.198 | 1.98 |
| Boric Acid | 0.40 | 4.0 | 0.40 | 4.0 | 0.40 | 4.0 | 0.40 | 4.0 |
| Sodium Borate | 0.022 | 0.22 | 0.022 | 0.22 | 0.022 | 0.22 | 0.022 | 0.22 |
| Disodium Phosphate | 0.027 | 0.27 | 0.027 | 0.27 | 0.027 | 0.27 | 0.027 | 0.27 |
| Sodium Citrate Dihydrate | 0.40 | 4.0 | 0.40 | 4.0 | 0.40 | 4.0 | 0.40 | 4.0 |
| Sodium Chloride* | | | | | | | | |
| Potassium Chloride | 0.10 | 1.0 | 0.10 | 1.0 | 0.10 | 1.0 | 0.10 | 1.0 |
| 50% Aqueous Solution of Sodium Lactate | 0.057 | 0.57 | 0.057 | 0.57 | 0.057 | 0.57 | 0.057 | 0.57 |
| Magnesium Chloride | 0.013 | 0.13 | 0.013 | 0.13 | 0.013 | 0.13 | 0.013 | 0.13 |
| Glucose | 0.0036 | 0.036 | 0.0036 | 0.036 | 0.0036 | 0.036 | 0.0036 | 0.036 |
| Glycine | 0.00002 | 0.0002 | 0.00002 | 0.0002 | 0.00002 | 0.0002 | 0.00002 | 0.0002 |
| Ascorbic Acid | 0.00001 | 0.0001 | 0.00001 | 0.0001 | 0.00001 | 0.0001 | 0.00001 | 0.0001 |
| Disodium Edetate | 0.01 | 0.1 | 0.05 | 0.5 | 0.01 | 0.1 | 0.05 | 0.5 |
| Polyquaternium 42 (33% aqueous) | 0.0030 | 0.030 | 0.0015 | 0.015 | 0.0030 | 0.030 | 0.0015 | 0.015 |
| Sodium Chlorite Dihydrate | 0.014 | 0.14 | 0.014 | 0.14 | 0.014 | 0.14 | 0.014 | 0.14 |
| 1N Sodium Hydroxide solution** | | | | | | | | |
| 1N Hydrochloric Acid solution** | | | | | | | | |
| Purified Water*** | | | | | | | | |
| total | 100.00% | 1000.00 g | 100.00% | 1000.00 g | 100.00% | 1000.00 g | 100.00% | 1000.00 G |

*can be adjusted to tonicity of 280-290 mOsm/Kg
**can adjust to pH 7.2
***optionally, q.s to 100% w/w For Examples 8C-8D: The Sodium Hyaluronate can be supplied by CONTIPRO A.S. (DOLNI, DOBROUC, CZECH REPUBLIC)
For Examples 8C-8D: The Tamarind Seed Polysaccharide cab be supplied by INDENA (MILANO, ITALY).
For Examples 8A-8D: The Lemon Aspen Extract (Abacross™ *Acronychia acidula* fruit extract) can be supplied by SOUTHERN CROSS BOTANICALS (KNOCKROW NSW, AUSTRALIA).
For Examples 8A-8D: The Polysorbate 20 can be supplied by Merck KGaA (DARMSTADT, GERMANY).
For Examples 8A-8D: The Polysorbate 80 can be supplied by Merck KGaA (DARMSTADT, GERMANY).
For Examples 8C-8D: The Polyethylene Glycol 400 can be supplied by Clariant Produkte (BURGKIRCHEN, GERMANY).
For Examples 8A-8D: The Boric Acid can be supplied by Merck KGaA (DARMSTADT, GERMANY).
For Examples 8A-8D: The Sodium Borate can be supplied by Merck KGaA (DARMSTADT, GERMANY).
For Examples 8A-8D: The Sodium Chloride can be supplied by Caldic (DUSSELDORF, GERMANY).
For Examples 8A-8D: The Potassium Chloride can be supplied by Merck KGaA (DARMSTADT, GERMANY).
For Examples 8A-8D: The Hypromellose E3 2910 can be supplied by DOW CHEMICAL (PLAQUEMINE, LOUISIANA, USA).
For Examples 8A-8D: The Glycerin can be supplied by Emery Oleochemicals GmbH (DUSSELDORF, GERMANY).
For Examples 8A-8D: The Disodium Phosphate can be supplied by Merck KGaA (DARMSTADT, GERMANY).
For Examples 8A-8D: The Sodium Citrate can be supplied by Merck KGaA (DARMSTADT, GERMANY).
For Examples 8A-8D: The Sodium Lactate can be supplied as Sodium Lactate (50% aqueous) by Merck KGaA (DARMSTADT, GERMANY).
For Examples 8A-8D: The Glucose can be supplied by Roquette Freres (LASTREM, FRANCE).
For Examples 8A-8D: The Glycine can be supplied by Merck KGaA (DARMSTADT, GERMANY).
For Examples 8A-8D: The Ascorbic Acid can be supplied by DSM NUTRITIONAL Products (DRAKEMYRE, SCOTLAND, UK).
For Examples 8A-8D: The Polyquaternium 42 can be supplied as Polyquaternium 42 (33% aqueous) by DSM BIOMEDICAL, (BERKELEY, Calif.).
For examples 8A-8D: The Disodium Edetate can be supplied by Merck NV/SA (OVERUSE, BELGIUM).
For Examples 8A-8D: The 1N Sodium Hydroxide can be supplied by VWR (RADNER, Pa., USA).
For Examples 8A-8D: The 1N Hydrochloric acid can be supplied by VWR (RADNER, Pa., USA).
For Examples 8A-8D: The Sodium Chlorite Dihydrate can be supplied by Oxychem (WICHITA, Kans., USA)
Solution 8A can be prepared as follows:
1. To a 1500 ml beaker is added 800 grams of Purified Water USP.
2. To the above is added 10 g of Polysorbate 80 and 50 g of Polysorbate 20. The solution is mixed until both are fully mixed and dissolved.
3. To the above is added 1.0 g of Lemon Aspen Extract. The solution is mixed until the Lemon Aspen Extract is dissolved.
4. The solution is filtered through a 0.45 micron filter and returned to a 1500 ml beaker.
5. To the above is added 1.98 g of Hypromellose E3 Premium. The solution is mixed until the Hypromellose E3 Premium dissolved.
6. The following ingredients are next added sequentially, allowing each to dissolve before adding the next: 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.10 gram Disodium Edetate, 0.030 gram Polyquaternium-42 (33% aqueous), and 0.14 gram Sodium Chlorite.
7. The tonicity of the solution is determined and adjusted to 280 mOsm with Sodium Chloride.
8. The pH of the solution is measured and adjusted to 7.2 with 1N Sodium Hydroxide and/or 1N Hydrochloric acid.
9. The solution is brought to a volume of 1,000.00 grams with Purified Water and mixed for 10 minutes.
10. The solution is filtered using a 0.22 micron filter.
Solution 8B can be prepared as follows:
1. To a 1500 ml beaker is added 800 grams of Purified Water USP.
2. To the above is added 10 g of Polysorbate 80 and 50 g of Polysorbate 20. The solution is mixed until both are fully mixed and dissolved.
3. To the above is added 1.0 g of Lemon Aspen Extract. The solution is mixed until the Lemon Aspen Extract is dissolved.
4. The solution is filtered through a 0.45 micron filter and returned to a 1500 ml beaker.
5. To the above is added 1.98 g of Hypromellose E3 Premium. The solution is mixed until the Hypromellose E3 Premium dissolved.
6. The following ingredients are next added sequentially, allowing each to dissolve before adding the next: 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.05 gram Disodium Edetate, 0.015 gram Polyquaternium-42 (33% aqueous), and 0.14 gram Sodium Chlorite.
7. The tonicity of the solution is determined and adjusted to 280 mOsm with Sodium Chloride.
8. The pH of the solution is measured and adjusted to 7.2 with 1N Sodium Hydroxide and/or 1N Hydrochloric acid.
9. The solution is brought to a volume of 1,000.00 grams with Purified Water and mixed for 10 minutes.
10. The solution is filtered using a 0.22 micron filter.
Solution 8C can be prepared as follows:
1. To a 1500 ml beaker is added 800 grams of Purified Water USP.
2. To the above is added 2 g of Polysorbate 80 and 10 g of Polysorbate 20. The solution is mixed until both are fully mixed and dissolved.
3. To the above is added 0.1 g of Lemon Aspen Extract. The solution is mixed until the Lemon Aspen Extract is dissolved.
4. The solution is filtered through a 0.45 micron filter and returned to a 1500 ml beaker.
5. To the solution of Step 4 is added 1.2 grams of Sodium Hyaluronate. The solution is mixed to fully dissolve the Sodium Hyaluronate.

6. To the above is added 2.0 grams of Tamarind Seed Polysaccharide. The solution is mixed to fully dissolve the Tamarind Seed Polysaccharide.
7. To the above is added 1.98 g of Hypromellose E3 Premium. The solution is mixed until the Hypromellose E3 Premium dissolved.
8. The following ingredients are next added sequentially, allowing each to dissolve before adding the next: 2.50 grams Polyethylene Glycol 400, 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.10 gram Disodium Edetate, 0.030 gram Polyquaternium-42(33% aqueous), and 0.14 gram Sodium Chlorite.
9. The tonicity of the solution is determined and adjusted to 280 mOsm with Sodium Chloride.
10. The pH of the solution is measured and adjusted to 7.2 with 1N Sodium Hydroxide and/or 1N Hydrochloric acid.
11. The solution is brought to a volume of 1,000.00 grams with Purified Water and mixed for 10 minutes.
12. The solution is filtered using a 0.22 micron filter.

Solution 8D can be prepared as follows:
1. To a 1500 ml beaker is added 800 grams of Purified Water USP.
2. To the above is added 2 g of Polysorbate 80 and 10 g of Polysorbate 20. The solution is mixed until both are fully mixed and dissolved.
3. To the above is added 0.1 g of Lemon Aspen Extract. The solution is mixed until the Lemon Aspen Extract is dissolved.
4. The solution is filtered through a 0.45 micron filter and returned to a 1500 ml beaker.
5. To the solution of Step 4 is added 1.2 grams of Sodium Hyaluronate. The solution is mixed to fully dissolve the Sodium Hyaluronate.
6. To the above is added 2.0 grams of Tamarind Seed Polysaccharide. The solution is mixed to fully dissolve the Tamarind Seed Polysaccharide.
7. To the above is added 1.98 g of Hypromellose E3 Premium. The solution is mixed until the Hypromellose E3 Premium dissolved.
8. The following ingredients are next added sequentially, allowing each to dissolve before adding the next: 2.50 grams Polyethylene Glycol 400, 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.10 gram Disodium Edetate, 0.015 gram Polyquaternium-42 (33% aqueous), and 0.14 gram Sodium Chlorite.
9. The tonicity of the solution is determined and adjusted to 280 mOsm with Sodium Chloride.
10. The pH of the solution is measured and adjusted to 7.2 with 1N Sodium Hydroxide and/or 1N Hydrochloric acid.
11. The solution is brought to a volume of 1,000.00 grams with Purified Water and mixed for 10 minutes.
12. The solution is filtered using a 0.22 micron hydrophilic filter.

Example 9

Table 3 illustrates the components of formulations of the present invention (as illustrated in formulations 9A and 9B), which components can be incorporated as described below using conventional mixing technology.

TABLE 3

| INGREDIENT | 9A Useful for Relief of Dry Eye Irritation | | 9B Useful for Relief of Dry Eye Irritation | |
|---|---|---|---|---|
| | % w/w | amount per batch (gms) | % w/w | amount per batch (gms) |
| Sodium Hyaluronate | 0.20 | 2.0 | 0.10 | 1.0 |
| Tamarind Seed Polysaccharide | 0 | 0 | 0.20 | 2.0 |
| Lemon Aspen Extract | 0.01 | 0.1 | 0.10 | 1.0 |
| Polysorbate 80 | 0.2 | 2.0 | 1.0 | 10.0 |
| Polysorbate 20 | 1.0 | 10.0 | 5.0 | 50.0 |
| Polyethylene Glycol 400 | 0.25 | 2.5 | 0.25 | 2.5 |
| Boric Acid | 0.60 | 6.0 | 0.60 | 6.0 |
| Sodium Borate | 0.06 | 0.60 | 0.06 | 0.60 |
| Sodium Chloride* | | | | |
| Super refined Castor Oil | 0.625 | 6.25 | 0.625 | 6.25 |
| Lumuluse GRH-40 | 0.50 | 5.0 | 0.50 | 5.0 |
| Ethyl linolenate | 0.10 | 1.0 | 0 | 0 |
| Retinyl Palmitate | 0.05 | 0.5 | 0 | 0 |
| Polyquaternium 42 (33% aqueous) | 0.0045 | 0.045 | 0.0045 | 0.045 |
| 1N Sodium Hydroxide solution** | | | | |
| 1N Hydrochloric Acid solution** | | | | |
| Purified Water*** | | | | |
| total | 100.00% | 1000.0 g | 100.00% | 1000.0 g |

*can be adjusted to tonicity of 280-290 mOsm/Kg
**can adjust to pH 7.2
***optionally, q.s to 100% w/w For Examples 9A-9B: The Sodium Hyaluronate can be supplied by CONTIPRO A.S. (DOLNI, DOBROUC, CZECH REPUBLIC)
For Examples 9A-9B: The Lemon Aspen Extract (Abacross™ *Acronychia acidula* fruit extract) can be supplied by SOUTHERN CROSS BOTANICALS (KNOCKROW NSW, AUSTRALIA).
For Examples 9A-9B: The Polysorbate 20 can be supplied by Merck KGaA (DARMSTADT, GERMANY).
For Examples 9A-9B: The Polysorbate 80 can be supplied by Merck KGaA (DARMSTADT, GERMANY).
For Examples 9A-9B: The Polyethylene Glycol 400 can be supplied by Clariant Produkte (BURGKIRCHEN, GERMANY).
For Examples 9A-9B: The Boric Acid can be supplied by Merck KGaA (DARMSTADT, GERMANY).
For Examples 9A-9B: The Sodium Borate can be supplied by Merck KGaA (DARMSTADT, GERMANY).
For Examples 9A-9B: The Sodium Chloride can be supplied by Caldic (DUSSELDORF, GERMANY).
For Examples 9A-9B: The 1N Sodium Hydroxide can be supplied by VWR (RADNER, Pa., USA).
For Examples 9A-9B: The 1N Hydrochloric acid can be supplied by VWR (RADNER, Pa., USA).

For Examples 9A-9B: The Lumuluse GRH-40 is can be supplied by is supplied by VANTAGE (GURNEE, Ill., USA).
For Examples 9A-9B: The Super refined Castor Oil can be supplied by CRODA (EDISON, N.J., USA).
For Examples 9A-9B: The Ethyl linolenate can be supplied by SIGMA-ALDRICH (ST. LOUIS, Mo., USA).
For Examples 9A-9B: The Retinyl Palmitate can be supplied by SIGMA-ALDRICH (ST. LOUIS, Mo., USA).
For Examples 9A-9B: The Polyquaternium-42 (33% aqueous) can be supplied by DSM BIOMEDICAL (BERKELEY, Calif., USA).
For Example 9B: The Tamarind Seed Polysaccharide can be supplied by INDENA (MILAN, ITALY).
Solution 9A can be prepared as follows:
1. To a 50 ml beaker is added 5.0 grams of Lumuluse GRH-40
2. While mixing, 6.25 grams of Super refined Castor Oil is added.
3. Next is added 1 gram of Ethyl linolenate and 0.5 gram of Retinyl Palmitate to mix until uniform.
4. In a separate 1500 ml beaker is added 500 grams of Purified Water.
5. To the above is added 2 g of Polysorbate 80 and 10 g of Polysorbate 20. The solution is mixed until both are fully dissolved.
6. To the above is added 0.1 gram of Lemon Aspen Extract. The solution is mixed until the Lemon Aspen Extract is dissolved.
7. The solution is filtered through a 0.45 micron filter and returned to a 1500 ml beaker.
8. To the solution in step 7 is added 2.0 grams of Sodium Hyaluronate. The solution is mixed to fully dissolve the Sodium Hyaluronate.
9. The following ingredients are next added sequentially, allowing for each to dissolve before adding the next: 2.5 grams Polyethylene Glycol 400, 6.0 grams Boric acid, 0.06 gram Sodium Borate, and grams of Polyquaternium-42 (33% aqueous).
10. The contents of step 3 are added and mixed until uniform using a homogenizer.
11. The tonicity of the formula is determined and adjusted to 280 mOsm/Kg with Sodium Chloride.
12. The pH of the formula is adjusted to pH of 7.2 using the 1N Sodium Hydroxide and/or 1N Hydrochloric acid.
13. The solution is brought to 1000.0 grams using Purified Water USP and mixed for 10 minutes until fully uniform.
14. The solution is filtered using a 0.22 micron filter.
Solution 9B can be prepared as follows:
1. To a 50 ml beaker is added 5.0 grams of Lumuluse GRH-40
2. While mixing, 6.25 grams of Super refined Castor Oil is added.
3. The uniform solution is set aside for future use.
4. In a separate 1500 ml beaker is added 500 grams of Purified Water.
5. To the above is added 10 g of Polysorbate 80 and 50 g of Polysorbate 20. The solution is mixed until both are fully dissolved.
6. To the above is added 1.0 gram of Lemon Aspen Extract. The solution is mixed until the Lemon Aspen Extract is dissolved.
7. The solution is filtered through a 0.45 micron filter and returned to a 1500 ml beaker.
8. To the solution in step 7 is added 1.0 grams of Sodium Hyaluronate. The solution is mixed to fully dissolve the Sodium Hyaluronate.
9. Next, 2.0 grams of Tamarind Seed Polysaccharide is added. The solution is mixed to fully dissolve the Tamarind Seed Polysaccharide.
10. The following ingredients are next added sequentially, allowing for each to dissolve before adding the next: 2.5 grams Polyethylene Glycol 400, 6.0 grams Boric acid, 0.06 gram Sodium Borate, and 0.045 grams of Polyquaternium-42 (33% aqueous).
11. The contents of step 3 are added and mixed until uniform using a homogenizer.
12. The tonicity of the formula is determined and adjusted to 280 mOsm/Kg with Sodium Chloride.
13. The pH of the formula is adjusted to pH of 7.2 using the 1N Sodium Hydroxide and/or 1N Hydrochloric acid.
14. The solution is brought to 1000.0 grams using Purified Water USP and mixed for 10 minutes until fully uniform.
15. The solution is filtered using a 0.22 micron filter.

Example 10

Table 4 illustrates the components of formulations of the present invention (as illustrated in formulations 10A and 10B), which components can be incorporated as described below using conventional mixing technology.

TABLE 4

| INGREDIENT | 10A Useful for Relief of Dry Eye Irritation | | 10B Useful for Relief of Dry Eye Irritation for Contact Lenses | |
| --- | --- | --- | --- | --- |
| | % w/w | amount per batch (gms) | % w/w | amount per batch (gms) |
| Sodium Hyaluronate | 0.30 | 3.0 | 0.15 | 1.5 |
| Actinomyces Extract | 5.0 | 50.0 | 0 | 0 |
| Compound 1**** | 0 | 0 | 5.0 | 50.0 |
| Polysorbate 80 | 1.0 | 10.0 | 1.0 | 10.0 |
| Polysorbate 20 | 10.0 | 100.0 | 7.5 | 75.0 |
| Polyethylene Glycol 400 | 0.25 | 2.5 | 0 | 0 |
| Boric Acid | 0.60 | 6.0 | 0.60 | 6.0 |
| Sodium Borate | 0.05 | 0.50 | 0.05 | 0.50 |
| Sodium Chloride* | | | | |
| Potassium Chloride | 0.10 | 1.0 | 0.10 | 1.0 |
| Calcium Chloride Dihydrate | 0.006 | 0.06 | 0.006 | 0.06 |
| Magnesium Chloride | 0.006 | 0.06 | 0.006 | 0.06 |
| Sodium Chlorite Dihydrate | 0.014 | 0.14 | 0.014 | 0.14 |
| Polyquaternium 42 (33% aqueous) | 0.0015 | 0.015 | 0.0015 | 0.015 |
| Sodium Chlorite Dihydrate | 0.014 | 0.14 | 0.014 | 0.14 |
| 1N Sodium Hydroxide solution** | | | | |
| 1N Hydrochloric Acid solution** | | | | |
| Purified Water*** | | | | |
| total | 100.00% | 1000.0 g | 100.00% | 1000.00 g |

*adjust to tonicity of 280-290 mOsm/Kg
**adjust to pH 7.2
***q.s to 100% w/w
****(2E,4E,6E)-7-(1,1,2,2,3,3-hexamethyl-2,3-dihydro-1H-inden-5-yl)-3-methylocta-2,4,6-trienoic acid For Examples 10A-10B: The Sodium Hyaluronate can be supplied by CONTIPRO A.S. (DOLNI, DOBROUC, CZECH REPUBLIC)
For Example 10A: The *Actinomyces* species A5640 Extract (IHVR collection bacteria extract labeled under IHVR collection nomenclature as IHVR_39565_F7), can be supplied by Baruch S. Blumberg Institute, Doylestown, Pa.
For Example 10B: Compound 1 can be supplied by Sigma-Aldrich.
For Examples 10A-10B: The Polysorbate 20 can be supplied by Merck KGaA (DARMSTADT, GERMANY).
For Examples 10A-10B: The Polysorbate 80 can be supplied by Merck KGaA (DARMSTADT, GERMANY).
For Examples 10A: The Polyethylene Glycol 400 can be supplied by Clariant Produkte (BURGKIRCHEN, GERMANY).
For Examples 10A-10B: The Boric Acid can be supplied by Merck KGaA (DARMSTADT, GERMANY).
For Examples 10A-10B: The Sodium Borate can be supplied by Merck KGaA (DARMSTADT, GERMANY).
For Examples 10A-10B: The Sodium Chloride can be supplied by Caldic (DUSSELDORF, GERMANY).
For Examples 10A-10B: The Potassium Chloride can be supplied by Merck KGaA (DARMSTADT, GERMANY).
For Examples 10A-10B: The Calcium Chloride Dihydrate can be supplied by Merck KGaA (DARMSTADT, GERMANY).
For Examples 10A-10B: The Magnesium Chloride to be supplied can KGaA (DARMSTADT, GERMANY).
For Examples 10A-10B: The Polyquaternium-42 (33% aqueous) can be supplied by DSM BIOMEDICAL (BERKELEY, Calif., USA).
For Examples 10A-10B: The Sodium Chlorite Dihydrate can be supplied by Oxychem (WICHITA, Kans., USA)
For Examples 10A-10B: The 1N Sodium Hydroxide can be supplied by VWR (RADNER, Pa., USA).
For Examples 10A-10B: The 1N Hydrochloric acid can be supplied by VWR (RADNER, Pa., USA).
Solution 10A can be prepared as follows:
1. To a 1500 ml beaker is added 800 grams of Purified Water USP.
2. To the above is added 10 g of Polysorbate 80 and 100 g of Polysorbate 20. The solution is mixed until both are fully mixed and dissolved.
3. To the above is added 50.0 g of *Actinomyces* Extract. The solution is mixed until the *Actinomyces* Extract is dissolved.
4. The solution is filtered through a 0.45 micron filter and returned to a 1500 ml beaker.
5. To the solution of Step 4 is added 3.0 grams of Sodium Hyaluronate. The solution is mixed to fully dissolve the Sodium Hyaluronate.
6. The following ingredients are next added sequentially, allowing for each to dissolve before adding the next: 2.5 grams Polyethylene Glycol 400, 6.0 grams Boric acid, 0.05 gram Sodium Borate, 1.0 gram Potassium Chloride, 0.06 gram Calcium Chloride Dihydrate, 0.06 gram Magnesium Chloride, and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Solution 10B can be prepared as follows:
1. To a 1500 ml beaker is added 800 grams of Purified Water USP.
2. To the above is added 10 g of Polysorbate 80 and 75 g of Polysorbate 20. The solution is mixed until both are fully mixed and dissolved.
3. To the above is added 50.0 g of Compound I. The solution is mixed until the Compound I is dissolved.
4. The solution is filtered through a 0.45 micron filter and returned to a 1500 ml beaker.
5. To the solution of Step 4 is added 1.5 grams of Sodium Hyaluronate. The solution is mixed to fully dissolve the Sodium Hyaluronate.
6. The following ingredients are next added sequentially, allowing for each to dissolve before adding the next: 6.0 grams Boric acid, 0.05 gram Sodium Borate, 1.0 gram Potassium Chloride, 0.06 gram Calcium Chloride Dihydrate, 0.06 gram Magnesium Chloride and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Example 11

Table 5 illustrates the components of formulations of the present invention (as illustrated in formulations 11A and 11B), which components can be incorporated as described below using conventional mixing technology.

TABLE 5

| INGREDIENT | 11A Useful for Relief of Dry Eye Irritation for Contact Lenses | | 11B Useful for Relief of Dry Eye Irritation | |
| --- | --- | --- | --- | --- |
| | % w/w | amount per batch (gms) | % w/w | amount per batch (gms) |
| Sodium Hyaluronate | 0.120 | 1.20 | 0.120 | 1.20 |
| Tamarind Seed Polysaccharide | 0.200 | 2.00 | 0.200 | 2.00 |
| Actinomyces Extract | 5.0 | 50.0 | 0 | 0 |
| Compound 2**** | 0 | 0 | 0.5 | 5.0 |
| Polysorbate 80 | 1.0 | 10.0 | 1.0 | 10.0 |
| Polysorbate 20 | 10.0 | 100.0 | 3.0 | 30.0 |
| Polyethylene Glycol 400 | 0.25 | 2.5 | 0.25 | 2.5 |
| Glycerin | 0.25 | 2.5 | 0.25 | 2.5 |
| Hypromellose E3 2910 | 0.198 | 1.98 | 0.198 | 1.98 |
| Boric Acid | 0.40 | 4.0 | 0.40 | 4.0 |
| Sodium Borate | 0.022 | 0.22 | 0.022 | 0.22 |

TABLE 5-continued

| INGREDIENT | 11A Useful for Relief of Dry Eye Irritation for Contact Lenses | | 11B Useful for Relief of Dry Eye Irritation | |
|---|---|---|---|---|
| | % w/w | amount per batch (gms) | % w/w | amount per batch (gms) |
| Disodium Phosphate | 0.027 | 0.27 | 0.027 | 0.27 |
| Sodium Citrate Dihydrate | 0.40 | 4.0 | 0.40 | 4.0 |
| Sodium Chloride* | | | | |
| Potassium Chloride | 0.10 | 1.0 | 0.10 | 1.0 |
| 50% Aqueous Solution of Sodium Lactate | 0.057 | 0.57 | 0.057 | 0.57 |
| Magnesium Chloride | 0.013 | 0.13 | 0.013 | 0.13 |
| Glucose | 0.0036 | 0.036 | 0.0036 | 0.036 |
| Glycine | 0.00002 | 0.0002 | 0.00002 | 0.0002 |
| Ascorbic Acid | 0.00001 | 0.0001 | 0.00001 | 0.0001 |
| Disodium Edetate | 0.01 | 0.1 | 0.05 | 0.5 |
| Polyquaternium 42 (33% aqueous) | 0.0030 | 0.030 | 0.0015 | 0.015 |
| Sodium Chlorite Dihydrate | 0.014 | 0.14 | 0.014 | 0.14 |
| 1N Sodium Hydroxide solution** | | | | |
| 1N Hydrochloric Acid solution** | | | | |
| Purified Water*** | | | | |
| Total | 100.00% | 1000.00 g | 100.00 % | 1000.00 G |

*adjust to tonicity of 280-290 mOsm/Kg
**adjust to pH 7.2
***q.s to 100.00% volume
****4-(1-(1,1,2,2,3,3-hexamethyl-2,3-dihydro-1H-inden-5-yl)vinyl)benzoic acid For Examples 11A-11B: The Sodium Hyaluronate can be supplied by CONTIPRO A.S. (DOLNI, DOBROUC, CZECH REPUBLIC)
For Examples 11A-11B: The Tamarind Seed Polysaccharide can be supplied by INDENA (MILANO, ITALY).
For Example 11A: The *Actinomyces* species A5640 Extract (IHVR collection bacteria extract labeled under IHVR collection nomenclature as IHVR_39565_F7), can be supplied by Baruch S. Blumberg Institute, Doylestown, Pa.
For Example 11B: Compound 2 can be supplied by Sigma-Aldrich.
For Examples 11A-11B: The Polysorbate 20 can be supplied by Merck KGaA (DARMSTADT, GERMANY).
For Examples 11A-11B: The Polysorbate 80 can be supplied by Merck KGaA (DARMSTADT, GERMANY).
For Examples 11A-11B: The Polyethylene Glycol 400 can be supplied by Clariant Produkte (BURGKIRCHEN, GERMANY).
For Examples 11A-11B: The Boric Acid can be supplied by Merck KGaA (DARMSTADT, GERMANY).
For Examples 11A-11B: The Sodium Borate can be supplied by Merck KGaA (DARMSTADT, GERMANY).
For Examples 11A-11B: The Sodium Chloride can be supplied by Caldic (DUSSELDORF, GERMANY).
For Examples 11A-11B: The Potassium Chloride can be supplied by Merck KGaA (DARMSTADT, GERMANY).
For Examples 11A-11B: The Hypromellose E3 2910 can be supplied by DOW CHEMICAL (PLAQUEMINE, LOUISIANA, USA).
For Examples 11A-11B: The Glycerin to be supplied can Emery Oleochemicals GmbH (DUSSELDORF, GERMANY).
For Examples 11A-11B: The Disodium Phosphate can be supplied by Merck KGaA (DARMSTADT, GERMANY).
For Examples 11A-11B: The Sodium Citrate can be supplied by Merck KGaA (DARMSTADT, GERMANY).
For Examples 11A-11B: The Sodium Lactate can be supplied as Sodium Lactate (50% aqueous) by Merck KGaA (DARMSTADT, GERMANY).
For Examples 11A-11B: The Glucose can be supplied by Roquette Freres (LASTREM, FRANCE).
For Examples 11A-11B: The Glycine can be supplied by Merck KGaA (DARMSTADT, GERMANY).
For Examples 11A-11B: The Ascorbic Acid can be supplied by DSM NUTRITIONAL Products (DRAKEMYRE, SCOTLAND, UK).
For Examples 11A-11B: The Polyquaternium 42 can be supplied as Polyquaternium 42 (33% aqueous) by DSM BIOMEDICAL, (BERKELEY, Calif.).
For examples 11A-11B: The Disodium Edetate can be supplied by Merck NV/SA (OVERUSE, BELGIUM).
For Examples 11A-11B: The 1N Sodium Hydroxide can be supplied by VWR (RADNER, Pa., USA).
For Examples 11A-11B: The 1N Hydrochloric acid can be supplied by VWR (RADNER, Pa., USA). For Examples 11A-11B: The Sodium Chlorite Dihydrate can be supplied by Oxychem (WICHITA, Kans., USA)
Solution 11A can be prepared as follows:
1. To a 1500 ml beaker is added 800 grams of Purified Water USP.
2. To the above is added 10 g of Polysorbate 80 and 100 g of Polysorbate 20. The solution is mixed until both are fully mixed and dissolved.
3. To the above is added 50 g of *Actinomyces* Extract. The solution is mixed until the *Actinomyces* Extract is dissolved.
4. The solution is filtered through a 0.45 micron filter and returned to a 1500 ml beaker.
5. To the solution of Step 4 is added 1.2 grams of Sodium Hyaluronate. The solution is mixed to fully dissolve the Sodium Hyaluronate.
6. To the above is added 2.0 grams of Tamarind Seed Polysaccharide. The solution is mixed to fully dissolve the Tamarind Seed Polysaccharide.
7. To the above is added 1.98 g of Hypromellose E3 Premium. The solution is mixed until the Hypromellose E3 Premium dissolved.
8. The following ingredients are next added sequentially, allowing each to dissolve before adding the next: 2.50 grams Polyethylene Glycol 400, 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.10 gram Disodium Edetate, 0.030 gram Polyquaternium-42(33% aqueous), and 0.14 gram Sodium Chlorite.
9. The tonicity of the solution is determined and adjusted to 280 mOsm with Sodium Chloride.

10. The pH of the solution is measured and adjusted to 7.2 with 1N Sodium Hydroxide and/or 1N Hydrochloric acid.
11. The solution is brought to a volume of 1,000.00 grams with Purified Water and mixed for 10 minutes. 12. The solution is filtered using a 0.22 micron filter.

Solution 11B can be prepared as follows:
1. To a 1500 ml beaker is added 800 grams of Purified Water USP.
2. To the above is added 10 g of Polysorbate 80 and 30 g of Polysorbate 20. The solution is mixed until both are fully mixed and dissolved.
3. To the above is added 5.0 g of Compound I. The solution is mixed until the Compound I is dissolved.
4. The solution is filtered through a 0.45 micron filter and returned to a 1500 ml beaker.
5. To the solution of Step 4 is added 1.2 grams of Sodium Hyaluronate. The solution is mixed to fully dissolve the Sodium Hyaluronate.
6. To the above is added 2.0 grams of Tamarind Seed Polysaccharide. The solution is mixed to fully dissolve the Tamarind Seed Polysaccharide.
7. To the above is added 1.98 g of Hypromellose E3 Premium. The solution is mixed until the Hypromellose E3 Premium dissolved.
8. The following ingredients are next added sequentially, allowing each to dissolve before adding the next: 2.50 grams Polyethylene Glycol 400, 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.10 gram Disodium Edetate, 0.015 gram Polyquaternium-42 (33% aqueous), and 0.14 gram Sodium Chlorite.
9. The tonicity of the solution is determined and adjusted to 280 mOsm with Sodium Chloride.
10. The pH of the solution is measured and adjusted to 7.2 with 1N Sodium Hydroxide and/or 1N Hydrochloric acid.
11. The solution is brought to a volume of 1,000.00 grams with Purified Water and mixed for 10 minutes.
12. The solution is filtered using a 0.22 micron hydrophilic filter.

EMBODIMENTS OF THE PRESENT INVENTION

1. A microemulsion composition for treating the eye comprising:
   i) a safe and effective amount of a compound and/or extract having retinol-like properties and/or benefits for use in treating the eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

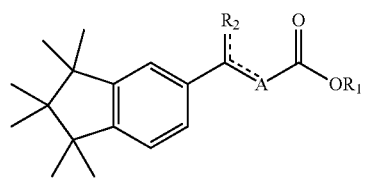

(I)

wherein—
   the dotted lines represent simple or double bound; optionally one of the dotted line is a double bound;
   $R_1$ represent an H, a carbonated chain, linear, cyclic, or branched, saturated or unsaturated, comprising from 1 to 20 carbon atoms;
   $R_2$ represent a carbonated chain, linear, cyclic ringed, or branched, saturated or unsaturated, comprising from 1 to 20 carbon atoms; optionally a methyl ($—CH_3$) or methylene ($=CH_2$) moiety; a carbonated chain, linear, ringed, or branched, saturated or unsaturated, comprising from 1 to 20 carbon atoms; optionally from 1 to 10 carbon atoms; optionally 6 carbon atoms; optionally an aromatic moiety, optionally a phenyl moiety; optionally 2-methyl-prop-1,3-diene.
   ii) an ophthalmologically acceptable carrier,
wherein the microemulsion droplets or particles have a maximum dimension of less than 1,500 Å.

2. The composition according to embodiment 1 (or, any of the following embodiments), wherein the compound and/or extract having retinol-like properties and/or benefits is a botanical extract, or source of extracts, from plants of the genus *Acronychia* and/or *Licaria*.

3. The composition according to embodiments 1 and/or 2 (or, any of the following embodiments), wherein the compound and/or extract having retinol-like properties and/or benefits is a botanical extract, or source of extracts, from plants of the genus *Acronychia*.

4. The composition according to anyone of, or a combination of, embodiments 1-3 (or, any of the following embodiments), wherein the botanical extract, or source of extracts, from plants of the genus *Acronychia* is selected from the group consisting of *Acronychia aberrans, Acronychia acidula, Acronychia acronychioides, Acronychia acuminate, Acronychia baeuerlenii, Acronychia chooreechillum, Acronychia crassipetala, Acronychia eungellensis, Acronychia imperforate, Acronychia laevis, Acronychia laurifolia, Acronychia littoralis, Acronychia oblongifolia, Acronychia octandra, Acronychia parviflora, Acronychia pauciflora, Acronychia pedunculata, Acronychia pubescens, Acronychia* species (Batavia Downs), *Acronychia suberosa, Acronychia vestita, Acronychia wilcoxiana*, and combinations of two or more thereof.

5. The composition according to anyone of, or a combination of, embodiments 1-4 (or, any of the following embodiments), wherein the botanical extract, or source of extracts, from plants of the genus *Acronychia* is *Acronychia acidula*.

6. The composition according to anyone of, or a combination of, embodiments 1-5 (or, any of the following embodiments), wherein the botanical extract of *Acronychia* and/or *Licaria* comprises from about 1% to about 20%, by weight of the extract, of the compound of Formula II

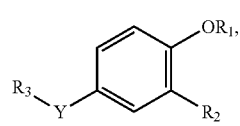

(II)

wherein:
R$_1$ is selected from the group consisting of C$_1$-C$_{20}$ alkyl, C$_2$-C$_{20}$ alkenyl, C$_2$-C$_{20}$ alkynyl, and C$_3$-C$_8$ cycloalkyl or aryl;
R$_2$ is selected from the group consisting of hydrogen, hydroxyl, C$_1$-C$_6$ alkyl, C$_2$-C$_6$ alkenyl, C$_2$-C$_6$ alkynyl, C$_3$-C$_8$ cycloalkyl or aryl, —OC$_1$-C$_6$ alkyl, —OC$_2$-C$_6$ alkenyl, —OC$_2$-C$_6$ alkynyl, —OC$_3$-C$_8$ cycloalkyl or aryl, thiol, —SC$_1$-C$_6$alkyl, —SC$_2$-C$_6$ alkenyl, —SC$_2$-C$_6$ alkynyl, —SC$_3$-C$_8$cycloalkyl or aryl, —NR$_4$C$_1$-C$_6$ alkyl, —NR$_4$C$_2$-C$_6$ alkenyl, —NR$_4$C$_2$-C$_6$ alkynyl, and —NR$_4$C$_3$-C$_8$cycloalkyl or aryl;
R$_3$ is selected from —CO$_2$H, —CO$_2$R$_4$ or an isosteric equivalent of a carboxy group, wherein R$_4$ is C$_1$-C$_6$ alkyl, C$_2$-C$_6$ alkenyl, C$_3$-C$_8$ cycloalkyl or aryl; and
Y is —(CH$_2$—CH$_2$)—, —(CH═CH)—, or —(C≡C)—.

7. The composition according to anyone of, or a combination of, embodiments 1-6 (or, any of the following embodiments), wherein the botanical extract of *Acronychia* and/or *Licaria* comprises from about 1% to about 20%, by weight of the extract, of the compound of Formula II

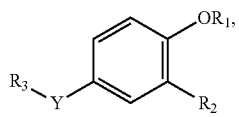
(II)

wherein:
R$_1$ is selected from the group consisting of C$_5$-C$_{16}$ alkyl, C$_5$-C$_{16}$ alkenyl, and C$_5$-C$_{16}$ alkynyl, more preferably C$_5$-C$_{16}$ alkenyl, including, for example, farnesyl;
R$_2$ is selected from the group consisting of hydrogen, hydroxyl, —OC$_1$-C$_6$alkyl, —OC$_2$-C$_6$alkenyl, —OC$_2$-C$_6$ alkynyl, —OC$_3$-C$_8$ cycloalkyl, more preferably hydrogen, hydroxyl, —OC$_1$-C$_6$ alkyl, even more preferably hydrogen or —OC$_1$-C$_3$ alkyl;
R$_3$ is selected from —CO$_2$H, —CO$_2$R$_4$ wherein R$_4$ is C$_1$-C$_6$ alkyl, or an isosteric equivalent of a carboxy group; and
Y is —(CH$_2$—CH$_2$)— or —(CH═CH)—.

8. The composition according to anyone of, or a combination of, embodiments 1-7 (or, any of the following embodiments), wherein the compound of formula (II) are in the form of an acid or alkylester selected from 3-(4-farnesyloxyphenyl)-propionic acid, 3-(4-farnesyloxy-3-hydroxyphenyl)-propionic acid, 3-(4-farnesyloxy-3-methoxyphenyl)-propionic acid, alkylesters thereof and combinations of two or more thereof.

9. The composition according to anyone of, or a combination of, embodiments 1-8 (or, any of the following embodiments), wherein the compound of Formula II useful in the present invention is 3-(4-farnesyloxyphenyl)-propionic acid and/or its ethyl ester.

10. The composition according to anyone of, or a combination of, embodiments 1-9 (or, any of the following embodiments), wherein the compound and/or extract having retinol-like properties and/or benefits is a botanical extract, or source of extracts, from plants of the genus *Licaria*.

11. The composition according to anyone of, or a combination of, embodiments 1-10 (or, any of the following embodiments), wherein the botanical extract, or source of extracts, from plants of the genus *Licaria* is selected from the group consisting of, *Licaria vernicosa, Licaria britoniana, Licaria canella, Licaria cubensis, Licaria velutina* and *Licaria triandra*, and combinations of two or more thereof.

12. The composition according to anyone of, or a combination of, embodiments 1-11 (or, any of the following embodiments), wherein the botanical extract, or source of extracts, from plants of the genus *Licaria* is *Licaria vernicosa*.

13. The composition according to anyone of, or a combination of, embodiments 1-12 (or, any of the following embodiments), wherein the compound and/or extract having retinol-like properties and/or benefits is a bacterial extract, or source of extracts, of the genus *Actinomyces*.

14. The composition according to anyone of, or a combination of, embodiments 1-14 (or, any of the following embodiments), wherein the compound and/or extract having retinol-like properties and/or benefits is a bacterial extract, or source of extracts, of the *Actinomyces* species A5640.

15. The composition according to anyone of, or a combination of, embodiments 1-14 (or, any of the following embodiments), wherein the compound and/or extract having retinol-like properties and/or benefits comprises the compound of Formula (I):

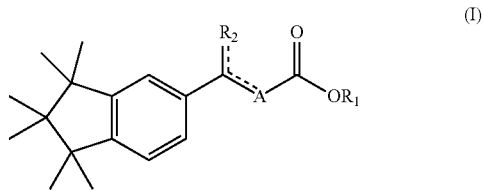
(I)

wherein—
the dotted lines represent simple or double bound; optionally, one of the dotted line is a double bound;
R$_1$ represent an H, a carbonated chain, linear, cyclic, or branched, saturated or unsaturated, comprising from 1 to 20 carbon atoms;
R$_2$ represent a carbonated chain, linear, cyclic ringed, or branched, saturated or unsaturated, comprising from 1 to 20 carbon atoms; a carbonated chain, linear, ringed, or branched, saturated or unsaturated, comprising from 1 to 20 carbon atoms.

16. The composition according to anyone of, or a combination of, embodiments 1-15 (or, any of the following embodiments), wherein the compound of Formula I is selected from (2E,4E,6E)-7-(1,1,2,2,3,3-hexamethyl-2,3-dihydro-1H-inden-5-yl)-3-methylocta-2,4,6-trienoic acid and 4-(1-(1,1,2,2,3,3-hexamethyl-2,3-dihydro-1H-inden-5-yl)vinyl)benzoic acid and their derivatives that display retinoid-like activity and mixtures thereof.

17. A method for preventing or treating the symptoms associated with dry eye (optionally, in a patient in need of such prevention and treatment) comprising the step of administering a microemulsion composition comprising:
i) a safe and effective amount of a compound and/or extract having retinol-like properties and/or benefits for use in treating dry eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

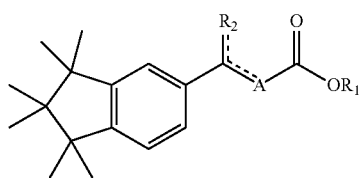

(I)

wherein—
the dotted lines represent simple or double bound;
R₁ represent an H, a carbonated chain, linear, cyclic, or branched, saturated or unsaturated, comprising from 1 to 20 carbon atoms;
R₂ represent a carbonated chain, linear, cyclic ringed, or branched, saturated or unsaturated, comprising from 1 to 20 carbon atoms; preferably a methyl (—CH₃) or methylene (=CH₂) moiety;
a represent a carbonated chain, linear, ringed, or branched, saturated or unsaturated, comprising from 1 to 20 carbon atoms; and
ii) optionally, an ophthalmologically acceptable carrier wherein the microemulsion droplets or particles have a maximum dimension of less than 1,500 Å.

18. A method for treating a patient having decreased or low-level production/release/delivery/excretion of hyaluronic acid and/or mucin from and/or in the cornea comprising the step of topically administering to the eye the patient a microemulsion composition comprising:
i) a safe and effective amount of a compound and/or extract having retinol-like properties and/or benefits for use in treating dry eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

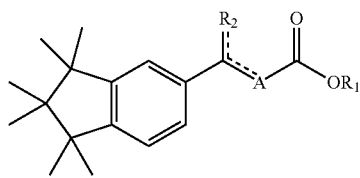

(I)

wherein—
the dotted lines represent simple or double bound; preferably one of the dotted line is a double bound;
R₁ represent an H, a carbonated chain, linear, cyclic, or branched, saturated or unsaturated, comprising from 1 to 20 carbon atoms;
R₂ represent a carbonated chain, linear, cyclic ringed, or branched, saturated or unsaturated, comprising from 1 to 20 carbon atoms; preferably a methyl (—CH₃) or methylene (=CH₂) moiety;
a represent a carbonated chain, linear, ringed, or branched, saturated or unsaturated, comprising from 1 to 20 carbon atoms; preferably from 1 to 10 carbon atoms; more preferably 6 carbon atoms; preferably an aromatic moiety, preferably a phenyl moiety; preferably 2-methyl-prop-1,3-diene.
ii) optionally, an ophthalmologically acceptable carrier wherein the microemulsion droplets or particles have a maximum dimension of less than 1,500 Å.

19. A method for treating dry eye comprising the step of topically administering to a patient a microemulsion composition comprising:
i) a safe and effective amount of a compound and/or extract having retinol-like properties and/or benefits for use in treating dry eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

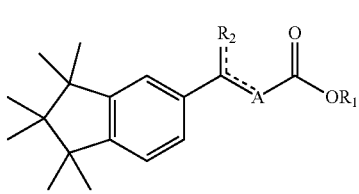

(I)

wherein—
the dotted lines represent simple or double bound; preferably one of the dotted line is a double bound;
R₁ represent an H, a carbonated chain, linear, cyclic, or branched, saturated or unsaturated, comprising from 1 to 20 carbon atoms;
R₂ represent a carbonated chain, linear, cyclic ringed, or branched, saturated or unsaturated, comprising from 1 to 20 carbon atoms; preferably a methyl (—CH₃) or methylene (=CH₂) moiety;
a represent a carbonated chain, linear, ringed, or branched, saturated or unsaturated, comprising from 1 to 20 carbon atoms; preferably from 1 to 10 carbon atoms; more preferably 6 carbon atoms; preferably an aromatic moiety, preferably a phenyl moiety; preferably 2-methyl-prop-1,3-diene;
ii) one or more demulcents or soothing agents; and
iii) optionally, an ophthalmologically acceptable carrier wherein the microemulsion droplets or particles have a maximum dimension of less than 1,500 Å.

20. A method for promoting healing or increasing the rate of healing of wounds in and/or on the eye (optionally, in a patient in need of such promoted healing or increased healing rate) by administering a microemulsion composition comprising:
i) a safe and effective amount of a compound and/or extract having retinol-like properties and/or benefits for use in treating dry eye selected from one or more of: botanical extracts, or sources of extracts, from plants of the genus *Acronychia, Licaria, Calendula* and/or *Trigonella*; bacterial extracts, or sources of extracts, of the genus *Actinomyces*; and compounds of Formula (I):

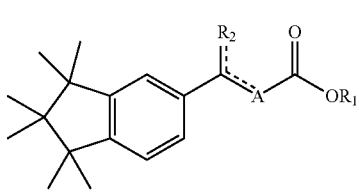

(I)

wherein—
the dotted lines represent simple or double bound; preferably one of the dotted line is a double bound;

R₁ represent an H, a carbonated chain, linear, cyclic, or branched, saturated or unsaturated, comprising from 1 to 20 carbon atoms;

R₂ represent a carbonated chain, linear, cyclic ringed, or branched, saturated or unsaturated, comprising from 1 to 20 carbon atoms; preferably a methyl (—CH₃) or methylene (=CH₂) moiety;

a represent a carbonated chain, linear, ringed, or branched, saturated or unsaturated, comprising from 1 to 20 carbon atoms; preferably from 1 to 10 carbon atoms; more preferably 6 carbon atoms; preferably an aromatic moiety, preferably a phenyl moiety; preferably 2-methyl-prop-1,3-diene.

ii) optionally, an ophthalmologically acceptable carrier wherein the microemulsion droplets or particles have a maximum dimension of less than 1,500 Å.

What is claimed is:

1. A microemulsion composition for treating the eye comprising:
i) a safe and effective amount of a compound and/or extract having retinol-like properties and/or benefits for use in treating the eye selected from one or more of: botanical extracts from plants of the genus *Acronychia*, *Licaria*, *Calendula* and/or *Trigonella*; bacterial extracts of the genus *Actinomyces*; and compounds of Formula (I):

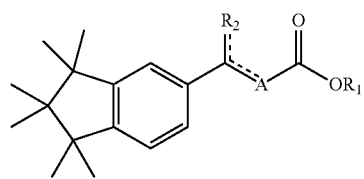

wherein—
the dotted lines represent simple or double bound; optionally one of the dotted line is a double bound;
R₁ represent an H, a carbonated chain, linear, cyclic, or branched, saturated or unsaturated, comprising from 1 to 20 carbon atoms;
R₂ represent a carbonated chain, linear, cyclic ringed, or branched, saturated or unsaturated, comprising from 1 to 20 carbon atoms;
optionally a methyl (—CH₃) or methylene (=CH₂) moiety; a carbonated chain, linear, ringed, or branched, saturated or unsaturated, comprising from 1 to 20 carbon atoms; optionally from 1 to 10 carbon atoms;
optionally 6 carbon atoms; optionally an aromatic moiety, optionally a phenyl moiety; optionally 2-methyl-prop-1,3-diene;
ii) an ophthalmologically acceptable carrier,
wherein the microemulsion droplets or particles have a maximum dimension of less than 1,500 Å.

2. The composition according to claim 1, wherein the compound and/or extract having retinol-like properties and/or benefits is a botanical extract from plants of the genus *Acronychia* and/or *Licaria*.

3. The composition according to claim 2, wherein the compound and/or extract having retinol-like properties and/or benefits is a botanical extract from plants of the genus *Acronychia*.

4. The composition according to claim 3, wherein the botanical extract from plants of the genus *Acronychia* is selected from the group consisting of *Acronychia aberrans*, *Acronychia acidula*, *Acronychia acronychioides*, *Acronychia acuminate*, *Acronychia baeuerlenii*, *Acronychia chooreechillum*, *Acronychia crassipetala*, *Acronychia eungellensis*, *Acronychia imperforate*, *Acronychia laevis*, *Acronychia laurifolia*, *Acronychia littoralis*, *Acronychia oblongifolia*, *Acronychia octandra*, *Acronychia parviflora*, *Acronychia pauciflora*, *Acronychia pedunculata*, *Acronychia pubescens*, *Acronychia* species (Batavia Downs), *Acronychia suberosa*, *Acronychia vestita*, *Acronychia wilcoxiana*, and combinations of two or more thereof.

5. The composition according to claim 4, wherein the botanical extract from plants of the genus *Acronychia* is *Acronychia acidula*.

6. The composition according to claim 2, wherein the botanical extract of *Acronychia* and/or *Licaria* comprises from about 1% to about 20%, by weight of the extract, of the compound of formula II

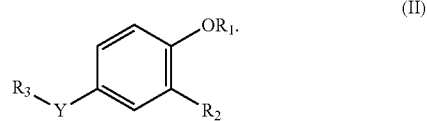

wherein:
R₁ is selected from the group consisting of $C_1$-$C_{20}$ alkyl, $C_2$-$C_{20}$ alkenyl, $C_2$-$C_{20}$ alkynyl, and $C_3$-$C_8$ cycloalkyl or aryl;
R₂ is selected from the group consisting of hydrogen, hydroxyl, $C_1$-$C_6$ alkyl, $C_2$-$C_6$ alkenyl, $C_2$-$C_6$ alkynyl, $C_3$-$C_8$ cycloalkyl or aryl, —O$C_1$-$C_6$ alkyl, —O$C_2$-$C_6$ alkenyl, —O$C_2$-$C_6$ alkynyl, —O$C_3$-$C_8$ cycloalkyl or aryl, thiol, —S$C_1$-$C_6$alkyl, —S$C_2$-$C_6$ alkenyl, —S$C_2$-$C_6$ alkynyl, —S$C_3$-$C_8$ cycloalkyl or aryl, —N$R_4$$C_1$-$C_6$ alkyl, —N$R_4$$C_2$-$C_6$ alkenyl, —N$R_4$$C_2$-$C_6$ alkynyl, and —N$R_4$$C_3$-$C_8$cycloalkyl or aryl;
R₃ is selected from —CO₂H, —CO₂R₄ or an isosteric equivalent of a carboxy group, wherein R₄ is $C_1$-$C_6$ alkyl, $C_2$-$C_6$ alkenyl, $C_3$-$C_8$ cycloalkyl or aryl; and
Y is —(CH₂—CH₂)—, —(CH=CH)—, or —(C≡C)—.

7. The composition according to claim 6, the botanical extract of *Acronychia* and/or *Licaria* comprises from about 1% to about 20%, by weight of the extract, of the compound of formula II

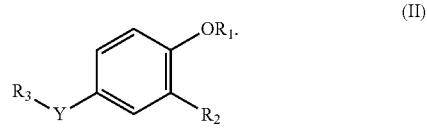

wherein:
R₁ is selected from the group consisting of $C_5$-$C_{16}$ alkyl, $C_5$-$C_{16}$ alkenyl, $C_5$-$C_{16}$ alkynyl, $C_5$-$C_{16}$ alkenyl, and farnesyl;
R₂ is selected from the group consisting of hydrogen, hydroxyl, —O$C_1$-$C_6$alkyl, —O$C_2$-$C_6$ alkenyl, —O$C_2$-$C_6$ alkynyl, —O$C_3$-$C_8$ cycloalkyl, hydrogen, hydroxyl, —O$C_1$-$C_6$ alkyl, and —O$C_1$-$C_3$ alkyl;
R₃ is selected from —CO₂H, —CO₂R₄ wherein R₄ is $C_1$-$C_6$ alkyl, or an isosteric equivalent of a carboxy group; and
Y is —(CH₂—CH₂)— or —(CH=CH)—.

8. The composition according to claim 7, wherein the compound of formula (II) are in the form of an acid or alkylester selected from 3-(4-farnesyloxyphenyl)-propionic acid, 3-(4-farnesyloxy-3-hydroxyphenyl)-propionic acid, 3-(4-farnesyloxy-3-methoxyphenyl)-propionic acid, alkylesters thereof and combinations of two or more thereof.

9. The composition according to claim 8, wherein the compound of Formula II is 3-(4-farnesyloxyphenyl)-propionic acid and/or its ethyl ester.

10. The composition according to claim 2, wherein the compound and/or extract having retinol-like properties and/or benefits is a botanical extract from plants of the genus *Licaria*.

11. The composition according to claim 10, wherein the botanical extract from plants of the genus *Licaria* is selected from the group consisting of, *Licaria vernicosa, Licaria brittoniana, Licaria canella, Licaria cubensis, Licaria velutina* and *Licaria triandra*, and combinations of two or more thereof.

12. The composition according to claim 11, wherein the botanical extract from plants of the genus *Licaria* is *Licaria vernicosa*.

13. The composition according to claim 1, wherein the compound and/or extract having retinol-like properties and/or benefits is a bacterial extract of the genus *Actinomyces*.

14. The composition according to claim 13, wherein the compound and/or extract having retinol-like properties and/or benefits is a bacterial extract of the *Actinomyces* species A5640.

15. The composition according to claim 1, wherein the compound and/or extract having retinol-like properties and/or benefits comprises the compound of Formula (I):

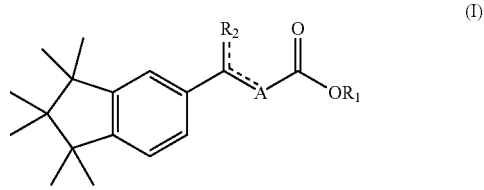

wherein— the dotted lines represent simple or double bound; optionally, one of the dotted line is a double bound;

$R_1$ represent an H, a carbonated chain, linear, cyclic, or branched, saturated or unsaturated, comprising from 1 to 20 carbon atoms;

$R_2$ represent a carbonated chain, linear, cyclic ringed, or branched, saturated or unsaturated, comprising from 1 to 20 carbon atoms; a carbonated chain, linear, ringed, or branched, saturated or unsaturated, comprising from 1 to 20 carbon atoms.

16. The composition according to claim 15, wherein the compound of Formula I is selected from (2E,4E,6E)-7-(1,1,2,2,3,3-hexamethyl-2,3-dihydro-1H-inden-5-yl)-3-methylocta-2,4,6-trienoic acid and 4-(1-(1,1,2,2,3,3-hexamethyl-2,3-dihydro-1H-inden-5-yl)vinyl)benzoic acid and mixtures thereof.

* * * * *